US012714721B2

(12) United States Patent
Baylink et al.

(10) Patent No.: US 12,714,721 B2
(45) Date of Patent: Aug. 25, 2026

(54) METHODS OF TREATMENT OF A CYTOKINE STORM

(71) Applicant: Loma Linda University Health, Loma Linda, CA (US)

(72) Inventors: David J. Baylink, Loma Linda, CA (US); Xiaolei Tang, Loma Linda, CA (US); Amir Abdipour, Loma Linda, CA (US); Samiksha Wasnik, Loma Linda, CA (US)

(73) Assignee: Loma Linda University Health, Loma Linda, CA (US)

( * ) Notice: Subject to any disclaimer, the term of this patent is extended or adjusted under 35 U.S.C. 154(b) by 0 days.

(21) Appl. No.: 17/928,972

(22) PCT Filed: Jun. 1, 2021

(86) PCT No.: PCT/US2021/070651
§ 371 (c)(1),
(2) Date: Dec. 1, 2022

(87) PCT Pub. No.: WO2021/248160
PCT Pub. Date: Dec. 9, 2021

(65) Prior Publication Data

US 2024/0050455 A1 Feb. 15, 2024

Related U.S. Application Data

(60) Provisional application No. 63/032,912, filed on Jun. 1, 2020, provisional application No. 63/102,168, filed on Jun. 1, 2020.

(51) Int. Cl.

| | |
|---|---|
| ***A61K 38/30*** | (2006.01) |
| ***A61K 31/131*** | (2006.01) |
| ***A61K 31/277*** | (2006.01) |
| ***A61K 31/375*** | (2006.01) |
| ***A61K 31/415*** | (2006.01) |
| ***A61K 31/69*** | (2006.01) |
| ***A61P 13/12*** | (2006.01) |
| ***A61P 37/06*** | (2006.01) |
| *A61P 11/00* | (2006.01) |

(52) U.S. Cl.
CPC ........... *A61K 31/69* (2013.01); *A61K 31/277* (2013.01); *A61K 31/375* (2013.01); *A61K 31/415* (2013.01); *A61K 38/30* (2013.01); *A61P 13/12* (2018.01); *A61P 37/06* (2018.01); *A61P 11/00* (2018.01)

(58) Field of Classification Search
CPC .... A61K 31/131; A61K 31/121; A61K 38/30; A61K 58/30; A61P 11/00; A61P 13/12
USPC ................................................. 514/627, 626
See application file for complete search history.

(56) References Cited

U.S. PATENT DOCUMENTS

2006/0293507 A1 12/2006 Schaffer et al.
2017/0197643 A1* 7/2017 Gariepy .............. G05D 1/0238

FOREIGN PATENT DOCUMENTS

WO 2018195308 10/2018
WO 2019125996 6/2019

OTHER PUBLICATIONS

Sartori, A. et al.: Teriflunomide : a novel oral treatment for relapsing multiple sclerosis. Exp. Opin. on Pharmacoth.; vol. 15, pp. 10-19-1027, 2014.*

(Continued)

*Primary Examiner* — Charanjit Aulakh
(74) *Attorney, Agent, or Firm* — Womble Bond Dickinson (US) LLP

(57) ABSTRACT

Provided here are methods for treating a cytokine storm in a subject. One such method includes the administration of a therapeutically effective amount of an Insulin-like Growth Factor (IGF-1), a $Ca^{2+}$-release-activated $Ca^{2+}$ (CRAC) channel inhibitor, or combinations thereof. Methods include treatment of acute lung injury or acute kidney injury with a therapeutically effective amount of 3,5-bis(trifluoromethyl) pyrazole derivative or teriflunomide, either individually or in combination with IGF-1.

4 Claims, 30 Drawing Sheets

Specification includes a Sequence Listing.

(56) References Cited

OTHER PUBLICATIONS

Popa, L. et al. : Pro-inflammatory signal delivered in vitro by Leflunomide active metabolite A771726 on abnormal peripheral monocytes in rheumatoid arthritis. Farmacia, vol. 58, pp. 546-558, 2010.*

International Search Report and Written Opinion for PCT Application No. PCT/US2021/070651, Sep. 1, 2021.

Gandhirajan et al. "Blockade of NOX2-and STIM1 signaling limits lipopolysaccharide-induced vascular inflammation," J Clin Invest, Feb. 1, 2013 (Feb. 1, 2013), vol. 123, pp. 887-902.

Mehrotra et al. "Calcium channel Orai1 promotes lymphocyte IL-17 expression and progressive kidney Injury," J Clin Invest, Nov. 1, 2019 (Nov. 1, 2019), vol. 129, pp. 4951-4961.

Rahman et al. "Unveiling some FDA-approved drugs as inhibitors of the store-operated Ca2+ entry pathway," Scientific Reports, Oct. 16, 2017 (Oct. 16, 2017), vol. 7, Article No. 12881, pp. 1-13.

Jairaman et al. "Molecular pharmacology of store-operated CRAC channels," Channels, Aug. 26, 2013 (Aug. 26, 2013), vol. 7, pp. 402-414.

Canna et al. "Making sense of the cytokine storm: a conceptual framework for understanding, diagnosing, and treating hemophagocytic syndromes," Pediatr Clin North Am, Apr. 1, 2012 (Apr. 1, 2012), vol. 59, pp. 1-20.

Munoz et al. "The Effects of Insulin-Like Growth Factor I and BTP-2 on Acute Lung Injury" Int. J. Mal. Sci, May 15, 2021 (May 15, 2021), vol. 22, 5244, pp. 1-17.

Wasnik et al. "IGF-1 Deficiency Rescue and Intracellular Calcium Blockade Improves Survival and Corresponding Mechanisms in a Mouse Model of Acute Kidney Injury," Int J Mot Sci, Jun. 8, 2020 (Jun. 8, 2020), vol. 21, 4095, pp. 1-17.

* cited by examiner

TLR 4
0.025
0.020
0.015
0.010
0.005
0.000

NFAT-1
0.03
0.02
0.01
0.00

Nf-kB
0.04
0.03
0.02
0.01
0.00

TRPC6
0.004
0.003
0.002
0.001
0.000

Orai 1
0.010
0.008
0.006
0.004
0.002
0.000
Relative Gene Expression (Normalized to GAPDH)
Healthy
LPS
LPS+IGF1
LPS+BTP2
LPS+IGF1+BTP2

IL-1b
0.004
0.003
0.002
0.001
0.000

IL-17
0.00330
0.00275
0.00220
0.00165
0.00110
0.00055
0.00000

IL-6
0.008
0.006
0.004
0.002
0.000

TNF-a
0.0030
0.0025
0.0020
0.0015
0.0010
0.0005
0.0000

IL-18
0.0012
0.0010
0.0008
0.0006
0.0004
0.0002
0.0000
Healthy
LPS
LPS+IGF1
LPS+BTP2
LPS+IGF1+BTP2
Relative gene expression (normalized to GAPDH)

SEQUENCE LISTING

```
<160> NUMBER OF SEQ ID NOS: 36

<210> SEQ ID NO 1
<211> LENGTH: 22
<212> TYPE: DNA
<213> ORGANISM: Artificial Sequence
<220> FEATURE:
<223> OTHER INFORMATION: TLR-4

<400> SEQUENCE: 1

gcctttcagg gaattaagct cc                                        22


<210> SEQ ID NO 2
<211> LENGTH: 21
<212> TYPE: DNA
<213> ORGANISM: Artificial Sequence
<220> FEATURE:
<223> OTHER INFORMATION: NFATC1
```

<400> SEQUENCE: 2
ggagagtccg agaatcgaga t 21

<210> SEQ ID NO 3
<211> LENGTH: 21
<212> TYPE: DNA
<213> ORGANISM: Artificial Sequence
<220> FEATURE:
<223> OTHER INFORMATION: TRPC6

<400> SEQUENCE: 3
gcttccgggg taatgaaaac a 21

<210> SEQ ID NO 4
<211> LENGTH: 19
<212> TYPE: DNA
<213> ORGANISM: Artificial Sequence
<220> FEATURE:
<223> OTHER INFORMATION: TRPC3

<400> SEQUENCE: 4
gccttcatgt tcggtgctc 19

<210> SEQ ID NO 5
<211> LENGTH: 22
<212> TYPE: DNA
<213> ORGANISM: Artificial Sequence
<220> FEATURE:
<223> OTHER INFORMATION: ORAI 1

<400> SEQUENCE: 5
ctcaactcgg tcaaagagtc ac 22

<210> SEQ ID NO 6
<211> LENGTH: 21
<212> TYPE: DNA
<213> ORGANISM: Artificial Sequence
<220> FEATURE:
<223> OTHER INFORMATION: CALCINEURIN

<400> SEQUENCE: 6
gtgaaagccg ttccatttcc a 21

<210> SEQ ID NO 7
<211> LENGTH: 22
<212> TYPE: DNA
<213> ORGANISM: Artificial Sequence
<220> FEATURE:
<223> OTHER INFORMATION: IL-1B

<400> SEQUENCE: 7
gaaatgccac cttttgacag tg 22

<210> SEQ ID NO 8
<211> LENGTH: 20
<212> TYPE: DNA
<213> ORGANISM: Artificial Sequence
<220> FEATURE:
<223> OTHER INFORMATION: IL-17

<400> SEQUENCE: 8
ggccctcaga ctacctcaac 20

<210> SEQ ID NO 9
<211> LENGTH: 21

<212> TYPE: DNA
<213> ORGANISM: Artificial Sequence
<220> FEATURE:
<223> OTHER INFORMATION: IL-6

<400> SEQUENCE: 9
ctgcaagaga cttccatcca g 21

<210> SEQ ID NO 10
<211> LENGTH: 19
<212> TYPE: DNA
<213> ORGANISM: Artificial Sequence
<220> FEATURE:
<223> OTHER INFORMATION: TNF-A

<400> SEQUENCE: 10
cctgtagccc acgtcgtag 19

<210> SEQ ID NO 11
<211> LENGTH: 21
<212> TYPE: DNA
<213> ORGANISM: Artificial Sequence
<220> FEATURE:
<223> OTHER INFORMATION: IFN-g

<400> SEQUENCE: 11
atgaacgcta cacactgcat c 21

<210> SEQ ID NO 12
<211> LENGTH: 21
<212> TYPE: DNA
<213> ORGANISM: Artificial Sequence
<220> FEATURE:
<223> OTHER INFORMATION: CD-31

<400> SEQUENCE: 12
ctgccagtcc gaaaatggaa c 21

<210> SEQ ID NO 13
<211> LENGTH: 23
<212> TYPE: DNA
<213> ORGANISM: Artificial Sequence
<220> FEATURE:
<223> OTHER INFORMATION: VEGF

<400> SEQUENCE: 13
gcacatagag agaatgagct tcc 23

<210> SEQ ID NO 14
<211> LENGTH: 21
<212> TYPE: DNA
<213> ORGANISM: Artificial Sequence
<220> FEATURE:
<223> OTHER INFORMATION: A-SMA

<400> SEQUENCE: 14
gtcccagaca tcagggagta a 21

<210> SEQ ID NO 15
<211> LENGTH: 21
<212> TYPE: DNA
<213> ORGANISM: Artificial Sequence
<220> FEATURE:
<223> OTHER INFORMATION: SP-D

<400> SEQUENCE: 15

```
ctcccactat cagaaagctg c                                              21


<210> SEQ ID NO 16
<211> LENGTH: 23
<212> TYPE: DNA
<213> ORGANISM: Artificial Sequence
<220> FEATURE:
<223> OTHER INFORMATION: CASPASE 3

<400> SEQUENCE: 16

atggagaaca acaaaacctc agt                                            23


<210> SEQ ID NO 17
<211> LENGTH: 23
<212> TYPE: DNA
<213> ORGANISM: Artificial Sequence
<220> FEATURE:
<223> OTHER INFORMATION: NGAL

<400> SEQUENCE: 17

gggaaatatg cacaggtatc ctc                                            23


<210> SEQ ID NO 18
<211> LENGTH: 19
<212> TYPE: DNA
<213> ORGANISM: Artificial Sequence
<220> FEATURE:
<223> OTHER INFORMATION: GAPDH

<400> SEQUENCE: 18

tggccttccg tgttcctac                                                 19


<210> SEQ ID NO 19
<211> LENGTH: 22
<212> TYPE: DNA
<213> ORGANISM: Artificial Sequence
<220> FEATURE:
<223> OTHER INFORMATION: TLR-4

<400> SEQUENCE: 19

gatcaaccga tggacgtgta aa                                             22


<210> SEQ ID NO 20
<211> LENGTH: 21
<212> TYPE: DNA
<213> ORGANISM: Artificial Sequence
<220> FEATURE:
<223> OTHER INFORMATION: NFATC1

<400> SEQUENCE: 20

ttgcagctag gaagtacgtc t                                              21


<210> SEQ ID NO 21
<211> LENGTH: 21
<212> TYPE: DNA
<213> ORGANISM: Artificial Sequence
<220> FEATURE:
<223> OTHER INFORMATION: TRPC6

<400> SEQUENCE: 21

gtatgctggt cctcgattag c                                              21


<210> SEQ ID NO 22
<211> LENGTH: 21
<212> TYPE: DNA
<213> ORGANISM: Artificial Sequence
```

<220> FEATURE:
<223> OTHER INFORMATION: TRPC3

<400> SEQUENCE: 22
ggtcacctcc agatgctcat t 21

<210> SEQ ID NO 23
<211> LENGTH: 21
<212> TYPE: DNA
<213> ORGANISM: Artificial Sequence
<220> FEATURE:
<223> OTHER INFORMATION: ORAI 1

<400> SEQUENCE: 23
cacgacctct gctaggaaaa g 21

<210> SEQ ID NO 24
<211> LENGTH: 23
<212> TYPE: DNA
<213> ORGANISM: Artificial Sequence
<220> FEATURE:
<223> OTHER INFORMATION: CALCINEURIN

<400> SEQUENCE: 24
gaatcgaagc accctctgtt att 23

<210> SEQ ID NO 25
<211> LENGTH: 21
<212> TYPE: DNA
<213> ORGANISM: Artificial Sequence
<220> FEATURE:
<223> OTHER INFORMATION: IL-1B

<400> SEQUENCE: 25
tggatgctct catcaggaca g 21

<210> SEQ ID NO 26
<211> LENGTH: 21
<212> TYPE: DNA
<213> ORGANISM: Artificial Sequence
<220> FEATURE:
<223> OTHER INFORMATION: IL-17

<400> SEQUENCE: 26
tctcgaccct gaaagtgaag g 21

<210> SEQ ID NO 27
<211> LENGTH: 23
<212> TYPE: DNA
<213> ORGANISM: Artificial Sequence
<220> FEATURE:
<223> OTHER INFORMATION: IL-6

<400> SEQUENCE: 27
agtggtatag acaggtctgt tgg 23

<210> SEQ ID NO 28
<211> LENGTH: 22
<212> TYPE: DNA
<213> ORGANISM: Artificial Sequence
<220> FEATURE:
<223> OTHER INFORMATION: TNF-A

<400> SEQUENCE: 28
gggagtagac aaggtacaac cc 22

<210> SEQ ID NO 29
<211> LENGTH: 21
<212> TYPE: DNA
<213> ORGANISM: Artificial Sequence
<220> FEATURE:
<223> OTHER INFORMATION: IFN-g

<400> SEQUENCE: 29
ccatcctttt gccagttcct c 21

<210> SEQ ID NO 30
<211> LENGTH: 20
<212> TYPE: DNA
<213> ORGANISM: Artificial Sequence
<220> FEATURE:
<223> OTHER INFORMATION: CD-31

<400> SEQUENCE: 30
cttcatccac cggggctatc 20

<210> SEQ ID NO 31
<211> LENGTH: 19
<212> TYPE: DNA
<213> ORGANISM: Artificial Sequence
<220> FEATURE:
<223> OTHER INFORMATION: VEGF

<400> SEQUENCE: 31
ctccgctctg aacaaggct 19

<210> SEQ ID NO 32
<211> LENGTH: 21
<212> TYPE: DNA
<213> ORGANISM: Artificial Sequence
<220> FEATURE:
<223> OTHER INFORMATION: A-SMA

<400> SEQUENCE: 32
tcggatactt cagcgtcagg a 21

<210> SEQ ID NO 33
<211> LENGTH: 23
<212> TYPE: DNA
<213> ORGANISM: Artificial Sequence
<220> FEATURE:
<223> OTHER INFORMATION: SP-D

<400> SEQUENCE: 33
cccacatctg tcatactcag gaa 23

<210> SEQ ID NO 34
<211> LENGTH: 23
<212> TYPE: DNA
<213> ORGANISM: Artificial Sequence
<220> FEATURE:
<223> OTHER INFORMATION: CASPASE 3

<400> SEQUENCE: 34
ttgctcccat gtatggtctt tac 23

<210> SEQ ID NO 35
<211> LENGTH: 21
<212> TYPE: DNA
<213> ORGANISM: Artificial Sequence
<220> FEATURE:
<223> OTHER INFORMATION: NGAL

```
<400> SEQUENCE: 35

catggcgaac tggttgtagt c                                              21


<210> SEQ ID NO 36
<211> LENGTH: 20
<212> TYPE: DNA
<213> ORGANISM: Artificial Sequence
<220> FEATURE:
<223> OTHER INFORMATION: GAPDH

<400> SEQUENCE: 36

gagttgctgt tgaagtcgca                                                20
```

METHODS OF TREATMENT OF A CYTOKINE STORM

TECHNICAL FIELD

The disclosure relates to methods and compositions containing an Insulin-like Growth Factor, a $Ca^{2+}$-release-activated $Ca^{2+}$ channel inhibitor, or a combination of both for addressing a cytokine storm for pre-exposure or post-exposure prophylactic or therapeutic benefit.

RELATED APPLICATIONS

This application is a U.S. National Phase Under 35 U.S.C. § 371 of International Application No. PCT/US2021/070651, titled "METHODS OF TREATMENT OF A CYTOKINE STORM," filed Jun. 1, 2021, which claims priority under applicable law of U.S. Provisional Patent Application No. 63/032,912 filed Jun. 1, 2020, and U.S. Provisional Patent Application No. 63/102,168 filed Jun. 1, 2020, the contents of which are incorporated herein by reference in their entirety and for all purposes.

SEQUENCE LISTING

The instant application contains a Sequence Listing which has been submitted electronically in .txt file format and is hereby incorporated by reference in its entirety. Said .txt copy, created on Jul. 19, 2023, is named LLU_20-025_144_8_ST25 and is 6,805 bytes in size. The Sequence Listing does not extend beyond the scope of the specification, and does not add new matter.

BACKGROUND

Cytokines play an important role in normal immune responses. A cytokine storm is an overreaction of the body's immune system that causes a release of tremendous amounts of cytokines. This storm can occur as a result of an infection, autoimmune condition, or other disease. A cytokine storm may lead to single or multiple organ failure and thus, have fatal effects. Acute lung injury (ALI) afflicts approximately 200,000 patients annually and has a 40% mortality rate. The coronavirus disease (COVID-19) pandemic has massively increased the rate of ALI incidence. The pathogenesis of ALI involves tissue damage from invading microbes and, in severe cases, the overexpression of inflammatory cytokines such as tumor necrosis factor-α (TNF-α) and interleukin-1β (IL-1β). Acute kidney injury (AKI) is a common disease in hospitalized elderly patients and has a high morbidity and mortality that results from intense inflammation. AKI can be caused by renal ischemia, nephrotoxicity or sepsis. The stage of AKI that is particularly detrimental to the patient is characterized by an increase in proinflammatory cytokines. COVID-19 is caused by a novel coronavirus that affects the upper and lower respiratory tract in the majority of cases. In certain cases, it results in a cytokine storm and results in the failure of organs, such as the lungs and the kidneys. Despite considerable effort, there continues to be a big need for therapeutic agents for these diseases brought about by the cytokine storm.

SUMMARY

Disclosed herein are compounds and methods addressing the shortcomings of the art, and may provide any number of additional or alternative advantages. Embodiments described herein include compositions and methods of treating a disease associated with a cytokine storm. Embodiments described herein include compositions and methods of reducing organ injury, improving organ function, and improving health outcomes.

One such method includes administering therapeutically effective amounts of an agent to decrease cytosolic calcium. The diseases can include one or more of traumatic or infectious conditions causing a cytokine storm or resulting in a cytokine storm. The diseases can include one or more of acute organ injuries due to infectious diseases, organ injuries, traumatic organ injuries, and surgical organ injuries disease. The diseases can include one or more of sepsis, massive injury, lung injury, AKI, or liver injury. In an embodiment, the disease can be an infectious disease, such as COVID-19. In certain instances, the cytokine storm is associated with coagulopathy. In an embodiment, the agent to decrease cytosolic calcium is a $Ca^{2+}$-release-activated $Ca^{2+}$ (CRAC) channel inhibitor. In an embodiment, the CRAC channel is a Store-operated CRAC (SOCC) channel. The CRAC channel inhibitor is a biological or a chemical agent. In an embodiment, the calcium channel inhibitor is an antibody directed to a CRAC channel. In an embodiment, the calcium channel inhibitor is a pyrazole derivative, such as 3,5-bis(trifluoromethyl)pyrazole derivative (BTP-2). In an embodiment, the calcium channel inhibitor is 2-Aminoethoxydiphenyl borate. In an embodiment, the agent to decrease cytosolic calcium is an inhibitor of pyrimidine synthesis. In an embodiment, the inhibitor of pyrimidine synthesis is teriflunomide.

Another embodiment of the method includes administering therapeutically effective amounts of Insulin-like Growth Factor (IGF-I) and an agent to decrease cytosolic calcium. In an embodiment, the agent to decrease cytosolic calcium is a CRAC channel inhibitor. In an embodiment, the CRAC channel is a SOCC channel. The CRAC channel inhibitor is a biological or a chemical agent. In an embodiment, the calcium channel inhibitor is an antibody directed to a CRAC channel. In an embodiment, the calcium channel inhibitor is a pyrazole derivative, such as BTP. In an embodiment, the calcium channel inhibitor is 2-Aminoethoxydiphenyl borate. In an embodiment, the agent to decrease cytosolic calcium is an inhibitor of pyrimidine synthesis. In an embodiment, the inhibitor of pyrimidine synthesis is teriflunomide.

Disclosed here are methods of administering IGF-I and Vitamin C to treat a disease caused by intense inflammation, such as a cytokine storm. In certain instances, the cytokine storm is associated with coagulopathy. In an embodiment, the disease is acute lung injury (ALI). In an embodiment, the disease is COVID-19. In an embodiment, the disease is AKI. Embodiments include methods for treating COVID-19 in a subject by administering to the subject a therapeutically effective amount of IGF-I, Vitamin C, and teriflunomide. Embodiments also include methods for treating COVID-19 in a subject by administering to the subject a therapeutically effective amount of IGF-I, Vitamin C, and BTP-2.

Embodiments include IGF-I, a CRAC channel inhibitor, or a combination of both for the manufacture of a medicament for treating ALI or AKI or a disease caused by a cytokine storm. Embodiments include a CRAC channel inhibitor for the manufacture of a medicament for treating ALI or AKI or a disease caused by a cytokine storm. Embodiments include teriflunomide for the manufacture of a medicament for treating ALI or AKI or a disease caused by a cytokine storm. Embodiments include IGF-I, a CRAC channel inhibitor, or a combination of both for use in treatment of ALI or AKI or a disease caused by a cytokine storm. Embodiments include a CRAC channel inhibitor for use in treatment of ALI or AKI or a disease caused by a cytokine storm. Embodiments include teriflunomide for use in treatment of ALI or AKI or a disease caused by a cytokine storm.

Embodiments described herein include compositions and methods of reducing organ injury, improving organ function, and improving health outcomes by administering IGF-I, a CRAC channel inhibitor, or a combination of both. These compositions can be administered as part of a pre-exposure or post-exposure prophylactic regimen or as a therapeutic regimen after injury. These compositions and methods disclosed herein can reduce injury to or improve the function of one or more organs, including muscles, heart, kidneys, liver, lungs, stomach, bladder, and intestines.

Numerous other aspects, features, and benefits of the present disclosure may be made apparent from the following detailed description taken together with the drawings. The treatment regimens can include compounds described herein, other components, or ingredients depending on desired prevention and treatment goals. It should be further understood that both the foregoing general description and the following detailed description are exemplary and explanatory, and are intended to provide further explanation of the inventions as claimed.

DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIG. 1A shows the serum IGF-I in the three groups of mice and FIG. 1B shows the correction of serum creatinine. IGF-I gene therapy normalized the low serum IGF-I and the high serum creatinine caused by LPS administration. Data are mean±SEM*p<0.05, p<0.01, **p<0.001 1-way ANOVA followed by a Dunnett's multiple comparisons test (n=3 in each group).

FIGS. 4A-4E show CD31 (PECAM) histology staining of renal sections, while FIGS. 4F-4J show α-SMA histology staining of renal sections. (original magnification 40×; Scale bar, 100 μm).

FIGS. 10A-10H are graphical representations of the relative mRNA expression of TLR 4 (FIG. 10A), TRPC3 (FIG. 10A), TRPC6 (FIG. 10A), Orai1 (FIG. 10A), Calcineurin (FIG. 10A), NFAT-1 (FIG. 10A), MAPK (FIG. 10A) and, Nf-κB (FIG. 10A), respectively. Day 7 RT-qPCR data are the mean±SEM. * p<0.05,  p<0.01, * p<0.001, and **** p<0.0001, ns-no significance. One-way ANOVA, followed by a Bonferroni's multiple comparisons test.

DETAILED DESCRIPTION

Figure 1A:
FIGS. 1A-1B are graphical representations of the serum IGF-I and the correction of serum creatinine in the healthy controls and Lipopolysaccharide (LPS)-treated animals following no treatment and treatment with IGF-1. LPS was administered i.p. on day 0, and the animals were sacrificed for measurements 7 days later. IGF-I gene therapy was given one day prior to LPS administration.

Reference will now be made to the exemplary embodiments illustrated in the drawings, and specific language will be used here to describe the same. It will nevertheless be understood that no limitation of the scope of the inventions is thereby intended. Alterations and further modifications of the inventive features illustrated here, and additional applications of the principles of the inventions as illustrated here, which would occur to one skilled in the relevant art and having possession of this disclosure, are to be considered within the scope of the inventions.

As used herein, unless otherwise noted, the terms "treating", "treatment" and the like, shall include the management and care of a subject or patient (preferably mammal, more preferably human) for the purpose of combating a disease, condition, or disorder and includes the administration of one or more chemical or biological agents to prevent the onset of the symptoms or complications, alleviate the symptoms or complications, arrest the development of clinical symptoms, cause regression of clinical symptoms, or eliminate the disease, condition, or disorder.

The term "therapeutically effective amount" as used herein, means that amount of active compound or chemical or biological agent that will bring about the desired response in a subject, such as reduction in symptoms, amelioration of inflammation, prevention of infection, protection against further injury, and elimination of existing inflammation or infection in a subject. The therapeutically effective amount will vary depending upon the subject and disease condition being treated, the weight and age of the subject, the severity of the disease condition, the manner of administration and the like, which can readily be determined by one of ordinary skill in the art. Illustratively, an effective amount of the compositions of this invention ranges from nanogram/kg to milligram/kg amounts for young children and adults. Equivalent dosages for lighter or heavier body weights can readily be determined.

Embodiments described herein include compositions and methods of reducing organ injury, improving organ function, and improving health outcomes by administering IGF-I, a CRAC channel inhibitor, or a combination of both. These compositions can be administered as part of a pre-exposure or post-exposure prophylactic regimen or as a therapeutic regimen after injury. These compositions and methods disclosed herein can reduce the injury to and/or improve the function of one or more organs, including muscles, heart, kidneys, liver, lungs, stomach, bladder, and intestines.

ALI often manifests as acute respiratory failure. ALI can occur from local or systemic causes and can result from infectious or noninfectious causes. Acute lung injury and acute respiratory distress syndrome (ARDS) are considered a continuum. With the pandemic of COVID-19, ALI is massively increased. ALI therapy is currently mainly supportive. Pathologically, both the alveolar epithelium and the vascular endothelium are injured in ALI. Additionally, there is a large increase in the serum and local expression of proinflammatory cytokines, particularly TNF-$\alpha$, IL-1$\beta$, interleukin-6 (IL-6), interleukin-8 (IL-8), and interleukin-18 (IL-18). The severity of ALI is influenced by neutrophil migration into the lungs in response to activated alveolar macrophages.

The treatment regimen was developed using IGF-I as one of the components. IGF-1 was selected because there was a reduction in serum IGF-I in sepsis and IGF-I is renal protective. The mechanism for the decrease in serum IGF-I in sepsis includes a depression of growth hormone receptor expression in the liver, which is a consequence of increased circulating inflammatory cytokines. The liver is the main source of circulating IGF-I. Additionally, IGF-I can cause proliferation and differentiation of renal tubular cells, and it modulates immune cells to reduce proinflammatory cytokine production. An AKI mouse model was used where AKI induced by parenteral injection of LPS. With systemic LPS administration, there is usually a component of vascular injury. IGF-I has several functions that counteract the effect of LPS to impair vascular function. In addition to its action as a regulator of cytosolic calcium, IGF-1 is also known for its reparative properties. IGF-1 increases endothelial adhesion molecules and increases proliferation of resident endothelial progenitor cells. IGF-1 increases the 1-$\alpha$-hydroxylase that produces 1, 25 vitamin D (which is vascular protective) and is important for the activation of sarco/endoplasmic reticulum $Ca^{2+}$-ATPase (SERCA). SERCA is an enzyme that regulates store operated calcium entry (SOCE), which in turn decreases the high cytosolic calcium typical of inflammatory conditions, including LPS administration. IGF-I has been shown to enhance the proliferation and differentiation of lung epithelial cells. IGF-I can modulate immune cells to reduce proinflammatory cytokine production. IGF-I has several functions that could counteract the harmful effects of infection on the vascular function. IGF-I is a pleiotropic growth factor and has been shown to improve lung tissue repair.

Embodiments of the methods disclosed herein include administering therapeutically effective amounts of IGF-I and an agent to decrease cytosolic calcium. In an embodiment, the agent to decrease cytosolic calcium is a CRAC channel inhibitor. In an embodiment, the CRAC channel is a SOCC channel. The CRAC channel inhibitor is a biological or a chemical agent. In an embodiment, the calcium channel inhibitor is an antibody directed to a CRAC channel. In an embodiment, the calcium channel inhibitor is a pyrazole derivative, such as BTP. In an embodiment, the calcium channel inhibitor is 2-Aminoethoxydiphenyl borate. In an embodiment, the agent to decrease cytosolic calcium is an inhibitor of pyrimidine synthesis. In an embodiment, the inhibitor of pyrimidine synthesis is teriflunomide.

Embodiments described herein include method of treating a disease associated with a cytokine storm. The diseases can include one or more of traumatic or infectious conditions causing a cytokine storm or resulting in a cytokine storm. The diseases can include one or more of acute organ injuries due to infectious diseases, organ injuries, traumatic organ injuries, and surgical organ injuries disease. The diseases can include one or more of sepsis, massive injury, lung injury, acute kidney injury (AKI), or liver injury. In an embodiment, the disease can be an infectious disease, such as COVID-19. In certain instances, the cytokine storm is associated with coagulopathy.

Vitamin C or Ascorbic acid supports vascular function. One of the major abnormalities to occur with cytokine storm and sepsis is a loss of vascular integrity. Ascorbic acid increases type IV collagen synthesis and promote endothelial cell proliferation, along with inhibiting apoptosis. It is also an antioxidant and therefore a radical scavenger. Ascorbic acid is known to prevent vascular permeability. Disclosed here are methods of administering IGF-I and Vitamin C to treat a disease caused by intense inflammation, such as a cytokine storm. The diseases can include one or more of traumatic or infectious conditions causing a cytokine storm or resulting in a cytokine storm. The diseases can include one or more of acute organ injuries due to infectious diseases, organ injuries, traumatic organ injuries, and surgical organ injuries disease. The diseases can include one or more of sepsis, massive injury, lung injury, AKI, or liver injury. In an embodiment, the disease can be an infectious disease, such as COVID-19. In certain instances, the cytokine storm is associated with coagulopathy. Embodiments include methods for treating COVID-19 in a subject by administering to the subject a therapeutically effective amount of IGF-I, Vitamin C, and teriflunomide. Embodiments also include methods for treating COVID-19 in a subject by administering to the subject a therapeutically effective amount of IGF-I, Vitamin C, and BTP-2. Embodiments include IGF-I, Vitamin C, and a CRAC channel inhibitor for use as a prophylaxis composition either pre-exposure and post-exposure to an infectious agent that causes ALI or AKI or a cytokine storm. Embodiments include IGF-I, Vitamin C, and teriflunomide for use as a prophylaxis composition either pre-exposure and post-exposure to an infectious agent that causes ALI or AKI or a cytokine storm. Providing IGF-I, Vitamin C, and a CRAC channel inhibitor as a part of pre-exposure and post-exposure regimen would positively affect vascular function, decrease organ injury, improving organ function, and improve survival.

Embodiments of the methods disclosed herein include administering therapeutically effective amounts of an agent to decrease cytosolic calcium. In an embodiment, the agent to decrease cytosolic calcium is a $Ca^{2+}$-release-activated $Ca^{2+}$ (CRAC) channel inhibitor. In an embodiment, the CRAC channel is a Store-operated CRAC (SOCC) channel. The CRAC channel inhibitor is a biological or a chemical agent. In an embodiment, the calcium channel inhibitor is an antibody directed to a CRAC channel. In an embodiment, the calcium channel inhibitor is a pyrazole derivative, such as 3,5-bis(trifluoromethyl)pyrazole derivative (BTP). In an embodiment, the calcium channel inhibitor is 2-Aminoethoxydiphenyl borate. In an embodiment, the agent to decrease cytosolic calcium is an inhibitor of pyrimidine synthesis. In an embodiment, the inhibitor of pyrimidine synthesis is teriflunomide.

The biological agents, such as the IGF-1, to treat the cytokine storm may be delivered via a gene therapy approach. The chemical and biological agents to treat the cytokine storm may be administered in either single or multiple doses by any of the accepted modes of administration, including by intra-arterial injection, intravenously, intraperitoneally, parenterally, intramuscularly, subcutaneously, orally, topically, as an inhalant, or via an impregnated or coated device or via rectal, buccal, intranasal and transdermal routes. In an embodiment, IGF-I can be administered parentally, intraperitoneally (i.p.), subcutaneously, intravenously, intramuscularly or intranasally. The appropriate dose is a dose sufficient to correct the deficiency seen in AKI. BTP-2 is given parenterally. The duration of therapies is sufficient to normalize the elevated serum cytokine.

LPS initiates its cellular toxicity by binding to and activating the TLR-4 complex, which leads to an increase in cytosolic calcium. The increase in cytosolic calcium mediates many of the adverse effects of LPS on the cellular functions. Several compositions of this disclosure were evaluated on two significant organs that sustained LPS-induced inflammatory injury. The treatment regimen was developed to include inhibitors of SOCE via inhibition of the CRAC/Orai1 channel, which leads to a decrease in cytosolic calcium.

Embodiments described herein include method of treating a disease associated with a cytokine storm by administering therapeutically effective amounts of one or more of IGF-I and a CRAC channel inhibitor. In the development of an example of a therapeutic regimen to treat a cytokine storm, such as AKI, IGF-I and a CRAC channel inhibitor were tested individually and in combination. BTP-2 and teriflunomide are two examples of SOCE inhibitors. The relevant gene expressions and histopathology evaluations determined the IGF-I and SOCE inhibitors individually and in combination provided beneficial therapeutic effects. For example, IGF-I, teriflunomide, and BTP-2, individually and the combination therapy, provide positive therapeutic actions.

Experiments were designed to focus on cytosolic calcium regulation as a significant factor in the damage caused by LPS and the improvement elicited by IGF-I and a CRAC channel inhibitor, individually and in combination. LPS causes increased cytosolic calcium in several different cell types, including immune cells, endothelial cells, and epithelial cells. BTP-2 has been shown to decrease the release of proinflammatory cytokines, indicating that the observed consequences to the BTP-2 treatment are calcium-dependent. However, improvements in tissue damage are not limited to the local actions of BTP-2 on a given tissue. Improvements in tissue damage by BTP-2 therapy could be due to a combination of the reduced proinflammatory cytokine, improved vascular function, or direct actions of BTP-2 on perturbed SOCE in various cells within the organ, including alveolar epithelial cells in the lungs. The BTP-2 treatment reduced LPS-induced ALI injury by influencing the cytosolic calcium signaling and regulatory processes. In particular, the BTP-2 treatment normalized LPS increases in Orai1, TRPC3, and TRPC6, an effect that is predicted to stabilize the cytosolic calcium and downstream transcriptional pathways. Accordingly, BTP-2 normalized LPS-mediated increases in calcineurin and Nfat1, which are activated downstream from the increases in the cytosolic calcium through ORAI, the TRPC channels, and the associated SOCE pathways. Critically, Nfat1 activation is coupled to proinflammatory cytokine production. IGF-1 is well-regarded for its pleiotropic effects on the cell functions; however, IGF-I's influence on cellular calcium is less well-known. Interestingly, as shown in the experiments here, IGF-1 had many parallel effects on BTP-2, where IGF-I caused a significant decrease in Orai1, TRPC3, and TRPC6, albeit these effects were more modest than those of BTP-2. Such data provided indirect evidence that IGF-I regulates SOCE. The IGF-I treatment also caused downstream changes in calcineurin and Nfat1 similar in magnitude to those seen in BTP-2. Therefore, it is reasoned that the IGF-I treatment is mediated, at least in part, through regulatory effects on the cytosolic calcium. IGF-I can induce IP3 in skeletal muscle and, therefore, could release ER calcium into the cytosol, an action that could increase cytosolic calcium.

One exciting mechanism with respect to LPS-induced inflammation is the increase in the TLR-4 complex, which is an initial effect of LPS-mediated toxicity, is decreased to normal after seven days following the SOCE inhibitor therapy, suggesting that the effect of this SOCE inhibitor may feed back into the immune cells to inhibit the stimulation of the inflammatory response once the cytosolic calcium is normal. The LPS-mediated ALI and AKI injury models were reminiscent of the multiorgan failure issues observed in COVID-19 patients. COVID-19-associated multiorgan failure is linked to impaired mitochondrial function and decreases in the tricarboxylic acid (TCA) cycle function. Often, such depression in mitochondrial energy production is coupled to dysregulation of the calcium overload. Although there were similarities between BTP-2 and IGF-1 on the calcium regulatory pathways examined, the pleiotropic nature of IGF-1 is less causal than BTP-2. The results led to the presumption that BTP-2's actions are mediated through its influence on cytosolic calcium signaling involving the Orai1- and TRPC-dependent pathways. IGF-1, in comparison, in addition to the influence on the calcium-dependent pathways, is known for its protective effects on the tissue in response to injury and its ability to promote damaged tissue repair through a myriad of mechanisms.

The overall approach for the therapeutic modalities disclosed here was to focus on three essential biologic processes of inflammation and repair-namely, (1) increased production of the proinflammatory cytokines, (2) impaired vascular function, and (3) improved repair (or less injury). The relevant gene expressions and histopathology evaluations determined the beneficial prophylactic and therapeutic effects of CRAC channel inhibitor, individually and in combination with IGF-1.

Thrombosis can be life-threatening complication of Covid-19. In order for thrombosis to occur there is activation of platelets mediated at least in part by SOCE. Embodiments herein include methods of treating thrombosis by administering therapeutically effective amounts of one or more of IGF-I and a SOCE inhibitor, such as BPT 2 and teriflunomide, and thereby prevent pathologic thrombosis.

After severe inflammation, a long-term complication is fibrosis. Shown herein is the effect of LPS, lipopolysaccharide, which is the agent from bacteria causing injury to tissue to cause tissue damage and fibrosis. Embodiments herein include methods of treating fibrosis by administering therapeutically effective amounts of one or more of IGF-I and a SOCE inhibitor, such as BPT 2 and teriflunomide, and thereby ameliorating or preventing fibrosis.

In the present study, all three IGF-I, BTP-2, and the combination therapies were remarkably suppressive of the expression of IL-1, IL-6, IL 17, TNF-α, and IFN-γ adverse inflammatory cytokines as compared to the LPS group. IGF-I was as effective as BTP-2 in suppressing cytokine expression in the lungs. These therapeutic changes are similar to those found in the kidney injury studies. However, the decrease in TNF-α gene expression was greater in the lungs than in the kidneys. TNF-α is known to have direct adverse effects on vascular pericytes, cells that promote vascular integrity. TNF-α and IFN-γ were normalized in the three therapeutic groups of CRAC channel inhibitor or IGF-1, individually and in combination. Interestingly, because among the proinflammatory cytokines, only TNF-α and IFN-γ synergistically promote cell death by pancytosis. This action on cell death would be expected to release damage-associated molecular patterns (DAMPs), which would promote a sterile inflammatory response, and the infectious inflammatory response of the microbes. Significant sources of TNF-α and IFN-γ are neutrophils and macrophages. In this regard, there was a marked invasion of immune cells characterized by a darkly stained nucleus and an eosinophilic cytoplasm, features typical of neutrophils and macrophages, in the animals receiving LPS without therapy.

LPS adversely affected the gene expression of CD31, VEGF, and caspase 3 in the lung tissue and was markedly improved by the three therapeutic groups. The quantitative immunocytochemistry of CD31 and α-SMA showed suppression with LPS and a significant increase in all the therapeutic groups. Thus, the therapies had a favorable effect on the parameters of the vascular integrity in the lungs.

In the ALI study here, the synthesis of antimicrobial protein neutrophil gelatinase-associated lipocalin-2 (LCN2 or NGAL) was significantly increased in the lungs in response to LPS. In all three therapeutic groups, there was a significant reduction of the elevated NGAL gene expression. SP-D is a marker of alveolar epithelial cell proliferation during acute lung injury. The SP-D gene expression was markedly decreased by LPS and completely corrected by all three therapies. There was a remarkable improvement in all three therapies. These parameters were incorporated into an injury score, which was almost normalized in all three therapeutic groups, particularly the combination therapy.

Embodiments disclosed here are directed to cytosolic calcium regulation as a significant factor in the damage caused by diseases and the improvement elicited by a CRAC channel inhibitor or IGF-1, individually and in combination. Embodiments include an Insulin-like Growth Factor (IGF-I), a CRAC channel inhibitor, or a combination of both for the manufacture of a medicament for treating ALI or AKI or a disease caused by a cytokine storm. Embodiments include a CRAC channel inhibitor for the manufacture of a medicament for treating ALI or AKI or a disease caused by a cytokine storm. Embodiments include teriflunomide for the manufacture of a medicament for treating ALI or AKI or a disease caused by a cytokine storm. Embodiments include an IGF-I) a CRAC channel inhibitor, or a combination of both for use in treatment of ALI or AKI or a disease caused by a cytokine storm. Embodiments include a CRAC channel inhibitor for use in treatment of ALI or AKI or a disease caused by a cytokine storm. Embodiments include teriflunomide for use in treatment of ALI or AKI or a disease caused by a cytokine storm. Embodiments include a CRAC channel inhibitor for use as a prophylaxis composition either pre-exposure and post-exposure to an infectious agent that causes ALI or AKI or a cytokine storm. Embodiments include teriflunomide for use as a prophylaxis composition either pre-exposure and post-exposure to an infectious agent that causes ALI or AKI or a cytokine storm.

EXAMPLES

It should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples and are not for the purpose of limitation thereof. Also, it will be appreciated that one or more of the following-described aspects, expressions of aspects, and/or examples, can be combined with any one or more of the other following-described aspects, expressions of aspects and/or examples. Certain exemplary aspects will now be described to provide an overall understanding of the principles of the structure, function, manufacture, and use of the systems and methods disclosed herein. One or more examples of these aspects are illustrated in the accompanying drawings.

Example 1

LPS delivered i.p. was used as a systemic model of AKI and studied in 5 groups of animals. LPS significantly reduced serum IGF-I and intramuscular IGF-I in vivo gene therapy rescued this deficiency. At the 7-day time point, a treatment regimen of IGF-I and a CRAC channel inhibitor caused a significant increase in survival, as all of the untreated animals died in 72 hours. The four pathways associated with inflammation, including increase in cytosolic calcium, elaboration of proinflammatory cytokines, impairment of vascular integrity and cell injury were adversely affected in renal tissue by LPS, using a sublethal dose of LPS. The expression of several genes was measured in each of the above pathways. The combined IGF-I and BTP-2 therapy caused favorable gene expression response in all four pathways in AKI. These pathways are also involved in other types of severe inflammation including, sepsis, acute respiratory distress syndrome and probably severe coronavirus infection.

AKI inflammation was associated with a decrease in serum IGF-I. This deficiency was rescued by expression of IGF-1. An in vivo gene therapy approach was utilized. A lentiviral vector engineered to express IGF-I was injected into skeletal muscle of the mice. Constant IGF-I production was designed because IGF binding protein 3, which normally binds to and stabilizes IGF-1 in serum, is expected to decrease. This decrease is due to liver growth receptor depression and therefore the free IGF-I, being a small molecule, is excreted in the urine. By using in vivo gene therapy approach, the free IGF-I is available to the sites of injury in the kidney.

Figure 1B:
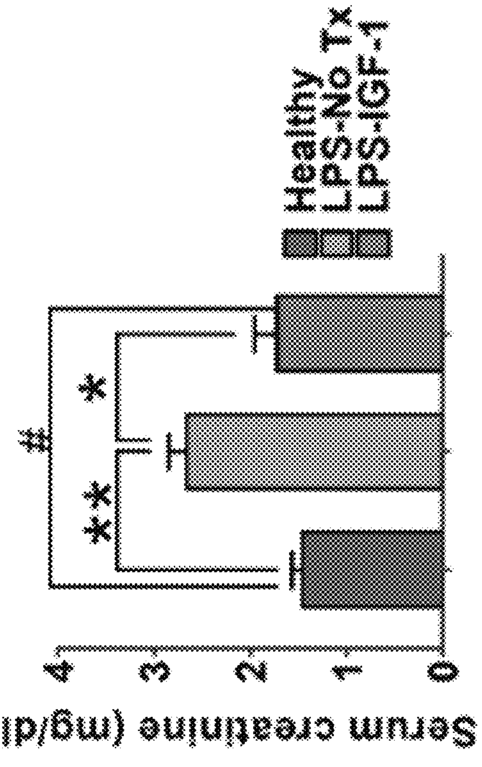

In this 7-day study, there was a marked drop in serum IGF-I from 337.5 to 85 ng/mL ($p<0.001$), as a consequence of LPS therapy (20 mg/kg body weight). Intramuscular injection of the Lenti-IGF-I vector rescued the serum IGF-I deficiency in the elevated serum creatinine (FIGS. 1A and 1B). Under normal conditions, IGF-I circulates bound to IGFBP3. However, under the conditions of LPS administration, IGFBP3 would be expected to be low. Consequently, IGF-1 produced by muscle should circulate as free IGF-I, which would be readily accessible through the remaining intact vasculature to the injured kidney.

Example 2

Figure 1C:
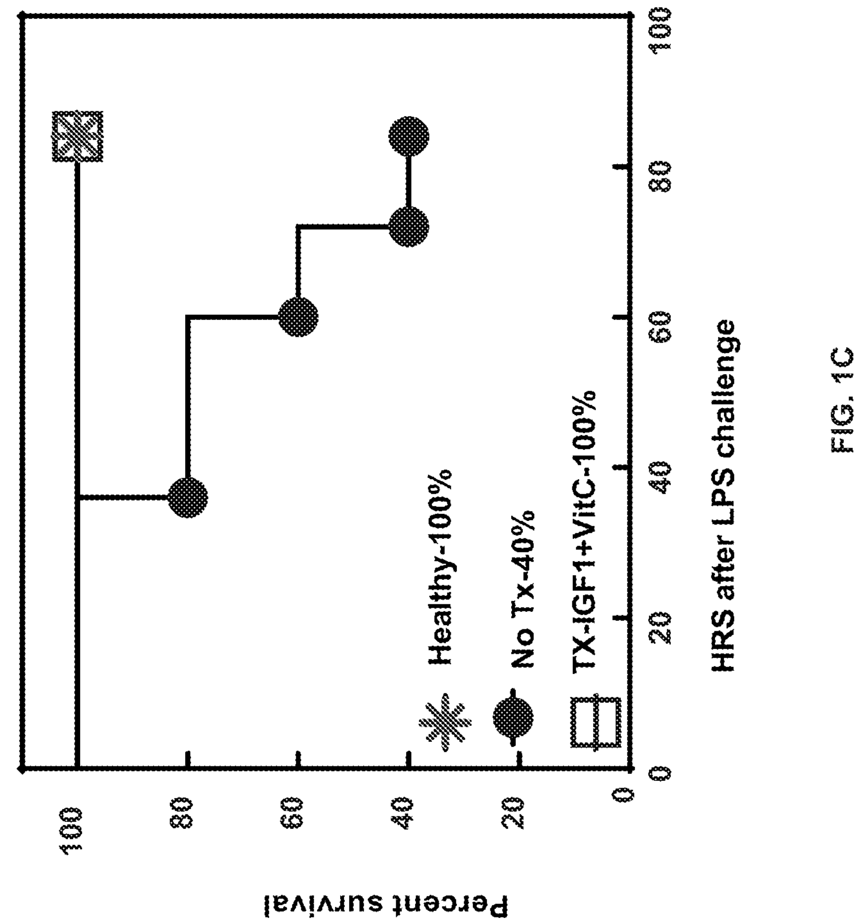
FIGS. 1C and 1D are graphical representations of the percentage of survival of LPS-treated animals following no treatment and treatment with different components of the treatment regimen, individually and in combination. All of the animals except the healthy group were treated with 25 mg/kg of LPS i.p. 144 hours post LPS injection. All of the surviving animals were sacrificed, and the experiment was terminated. Kaplan Meier survival in response to LPS administration. Comparison of the trend of survival curve was done using Log-rank (Mantel-Cox) test (recommended) test, and **** p<0.0001 (n=7 in each group).

Different components of the treatment regimen were tested, individually and in combination, for their effect on prolonging survival or affecting mortality. A survival test was performed with a lethal dose of LPS (25 mg/kg body weight). As LPS causes AKI, a mouse model was utilized where AKI was induced by parenteral injection of LPS. Animals were treated with IGF-1 and Vitamin C, individually and in combination to evaluate their effect on survival (FIG. 1C). Kaplan Meier survival analysis was conducted between LPS induced systemic-sepsis animals treated with or without IGF-1, Vitamin C or combination therapy measured over the 96 hour-study period. As shown in FIG. 1C, The overall survival rate was 40% in the LPS-No Tx and 100% in the LPS+IGF-1+VitC group at the end of the experiment at 96 hours. No mortality was observed among healthy mice.

Example 3

Figure 1D:
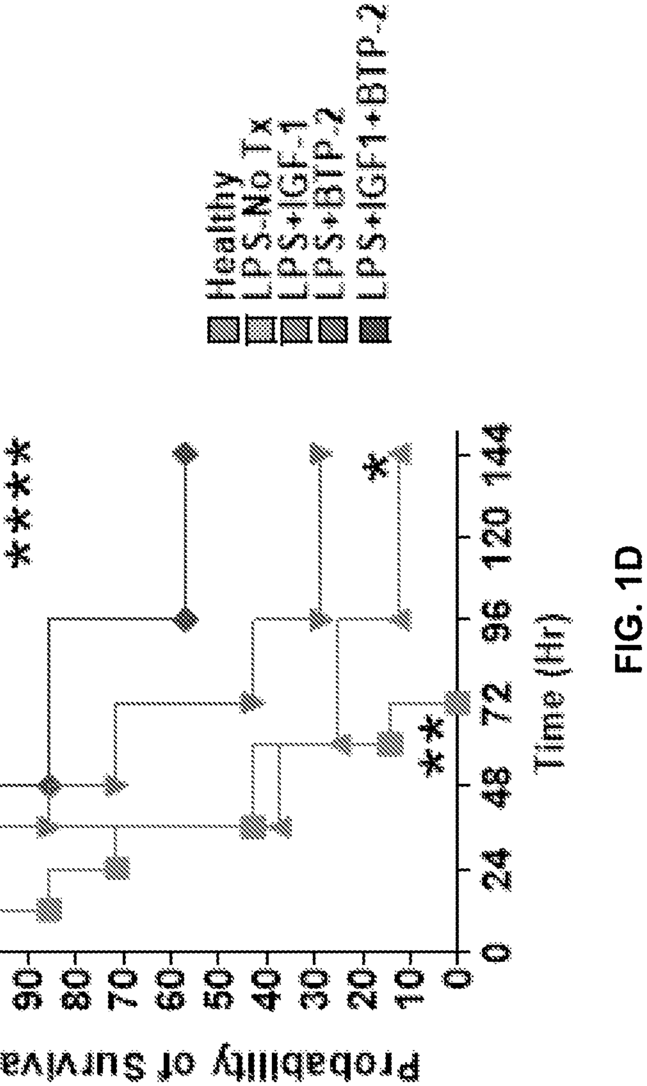

Different components of the treatment regimen were tested, individually and in combination, for their effect on prolonging survival or affecting mortality. A survival test was performed with a lethal dose of LPS (25 mg/kg body weight). Animals were treated with all components individually and in combination to evaluate their effect on survival. As LPS causes AKI, a mouse model was utilized where AKI was induced by parenteral injection of LPS. Pretreatment with IGF-1 monotherapy, BTP-2 monotherapy, and IGF-1+BTP-2 combination therapy was evaluated for effect in the mouse model to prevent the animals from succumbing to death due to organ failure in AKI. Mice (7 per groups) were i.p. injected with a lethal dose of LPS (25 mg/kg body weight). A group of mice received an i.p. injection of BTP-2 (16 mg/kg) one hour before LPS injection, and another group of mice received i.m. injection of Lenti-IGF1, 24 hours before LPS injection. A separate group of mice received a combination of IGF-1+BTP-2 as pretreatment. Mice were monitored every 6 hours. As shown in FIG. 1D, the mortality of mice treated only with LPS (labeled as LPS-No Tx) reached 58% within 36 hours and 100% within 72 hours. The mortality of LPS-injected mice that received an IGF-1 (labeled as LPS+IGF-1) pretreatment was 60% within 36 hours, and 88% at the end of the experiment (144 h). Mortality in LPS-injected mice that received BTP-2 (labeled as LPS+BTP-2) pretreatment was 0% within 36 hours, 30% within 48 hours and 72% at 144 hour-time point. However, the mortality in LPS-injected mice that received an IGF-1 and BTP-2 (labeled as LPS+IGF-1+BTP-2) pretreatment was comparatively low, which reached only 15% within 48 hours, and at the end of the 144 hour-time point reached only up to 43% (compared to LPS-No Tx). A lower mortality and higher survival rate in LPS+IGF-1+BTP-2 group, when compared to LPS-No Tx and monotherapies, demonstrates that it offers a survival advantage to LPS-induced AKI mice. The overall survival rate in LPS-No Tx was 0%, 12.5% in LPS+IGF-1, 28%, LPS+BTP-2 and 57% in LPS+IGF-1+BTP-2 groups at the end of the experiment (FIG. 1D). Meanwhile, no mortality was observed among mice treated with PBS, i.e., healthy group.

Example 4

Different components of the treatment regimen were tested, individually and in combination, for their effect on the key mechanisms associated with renal injury and repair. These mechanisms were studied by gene expression, histology and, in the case of vascular integrity, Evans blue leakage. Additionally, gene expression was evaluated for the processes of 1) intracellular calcium signaling, which is a major determine of inflammatory cytokines; 2) vascular leakage, which is in part due to inflammatory cytokines; and 3) renal injury, which is due to LPS toxicity and impaired vascularization.

Calcium Signaling

One of the earliest effects of LPS is to increase TLR-4 expression (FIG. 2A), which in turn increases Nfat—a transcription factor classically known to increase cytosolic calcium. The adverse action of LPS to produce AKI is heavily determined by aberrant calcium signaling. The downstream effect of Nfat has not been established for the kidney, but in lung microvasculature, LPS decreases ER calcium stores via an IP3 receptor mechanism. Emptying calcium stores increases calcium influx from the plasma membrane (SOCE) via Stim-1, which in turn promotes an increase in cytosolic calcium. Experiments were conducted to evaluate the expression of Stim-1 and Orai1 gene expression (or their analogues) as part of a mechanism to stimulate calcium reflux through the plasma membrane. In LPS-treated mice, there was a significant increase in Orai1 (FIG. 2E) but no change in Stim-1 (data not shown). The lack of a change in Stim-1 gene expression could have been related to the fact that gene expression of the total kidney but not individual cell types was measured. Different cell types express variable plasma membrane-associated calcium signaling mechanisms. In some cells, Stim stimulates a TRP channel, instead of or in addition to, Orai1. There was a significant increase in TRPC6, as well as Orai1, in response to LPS (FIG. 2D), both of which would be expected to increase cytosolic calcium.

Figures 2A, 2B, 2C, 2D, 2E:
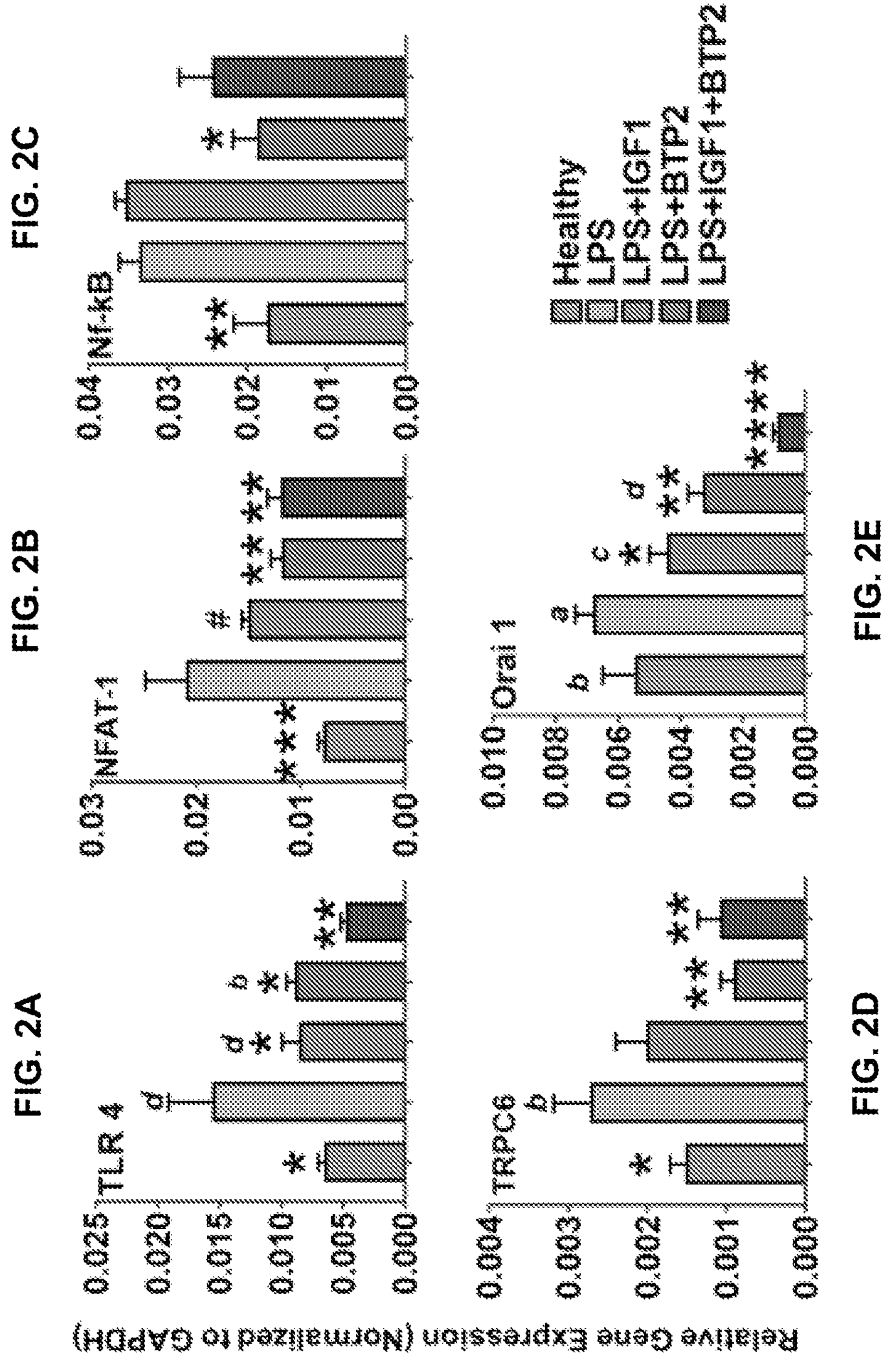
FIGS. 2A-2E are graphical representations of the relative gene expression of Toll-like receptor-4 (TLR 4), Nuclear factor of activated T-cells (NFAT-1), Nuclear factor kappa B (Nf-κB), TRPC6 (Transient Receptor Potential Cation Channel Subfamily C Member 6), and Orai1, respectively, in healthy controls, and LPS-treated animals following no treatment and treatment with different components of the treatment regimen, individually and in combination. The target for BTP-2 is Orai1, which is decreased by this therapeutic agent. Data are mean±SEM*p<0.05,  p<0.01, * p<0.001, **** p<0.0001 (* LPS Vs other groups) and d-p<0.05, c-p<0.01, b-p<0.001, α-p<0.0001 (LPS+IGF1+BTP2 vs other groups), 1-way ANOVA followed by a Dunnett's multiple comparisons test, (n=4 in each group).

Different components of the treatment regimen were tested, individually and in combination, for their effect on these LPS induced cytosolic metastatic calcium mechanisms. BTP-2 is a specific inhibitor of Orai1/SOCE, and LPS increased Orai1 expression, whereas importantly, BTP-2 monotherapy decreased Orai1 expression to normal (FIG. 2E). Interestingly, IGF-I monotherapy also decreased Orai1 expression (FIG. 2E). Actually, the combination therapy with IGF-I+BTP-2 decreased Orai1 to below normal (FIG. 2E), an effect which could have contributed to our observed increase in survival with combination therapy (FIG. 2E).

Inflammatory Gene Expression

Figures 3A, 3B, 3C, 3D, 3E:
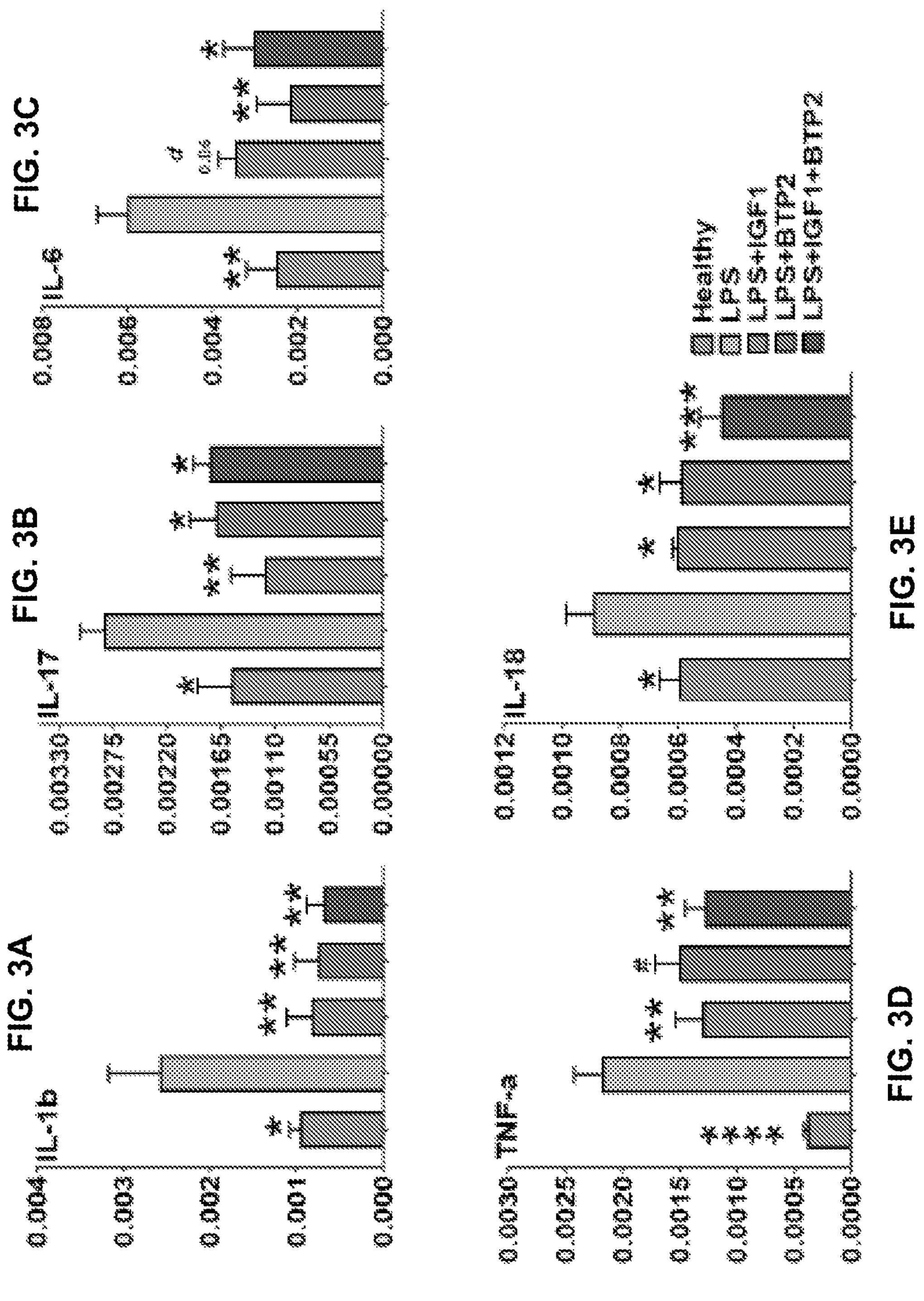
FIGS. 3A-3E are graphical representations of the relative gene expression of IL-1b, IL-17, IL-6, TNF-α, and IL-18, respectively, in healthy controls, and LPS-treated animals following no treatment and treatment with different components of the treatment regimen, individually and in combination. Data are mean±SEM*p<0.05,  p<0.01, * p<0.001, **** p<0.0001 (* LPS Vs other groups) and d-p<0.05, c-p<0.01, b-p<0.001, α-p<0.0001 (LPS+IGF1+BTP-2 Vs other groups)), 1-way ANOVA followed by a Dunnett's multiple comparisons test, (n=4 in each group).

The downstream effects of the treatment regimen on cytosolic calcium dynamics were evaluated. Elevated cytosolic calcium can lead to an increase in proinflammatory cytokines. Nfat and Nf-kB, which are cytosolic calcium-dependent, lead to an increase in proinflammatory cytokines, and both were increased in response to LPS, as shown in FIG. 2B and FIG. 2C, respectively. Nf-kB was decreased by BPT-2 therapy but not by combination therapy (FIG. 2C). Nf-kB increases the inflammatory cytokines, including IL-1β, IL-6, IL-18, the latter being especially important because it synergizes with other cytokines (FIGS. 3A, 3C, and 3E, respectively). Nfat enhances the differentiation of immune cell subsets that are associated with inflammation, such as Th1, Th2, and Th17 cells. Th17 cells express IL-17 (FIG. 3B), which can lead to maladaptive AKI repair. All of the cytokines were decreased by IGF-I, BTP-2 and the IGF-1+BTP-2 combination therapies (FIGS. 3A-3E). Inflammatory cytokines appear to directly contribute to the impaired vascular integrity seen with LPS treatment. Moreover, the cytokines also decrease the production of IGF-I in the liver and possibly locally at the inflamed sites in the kidney, which in turn has an adverse effect on vascular integrity. IL-18, which was also increased by LPS (FIG. 3E), is a product of the inflammasome, a calcium-dependent complex.

Vascular Integrity

Figures 4A, 4B, 4C, 4D, 4E, 4F, 4G, 4H, 4I, 4J:
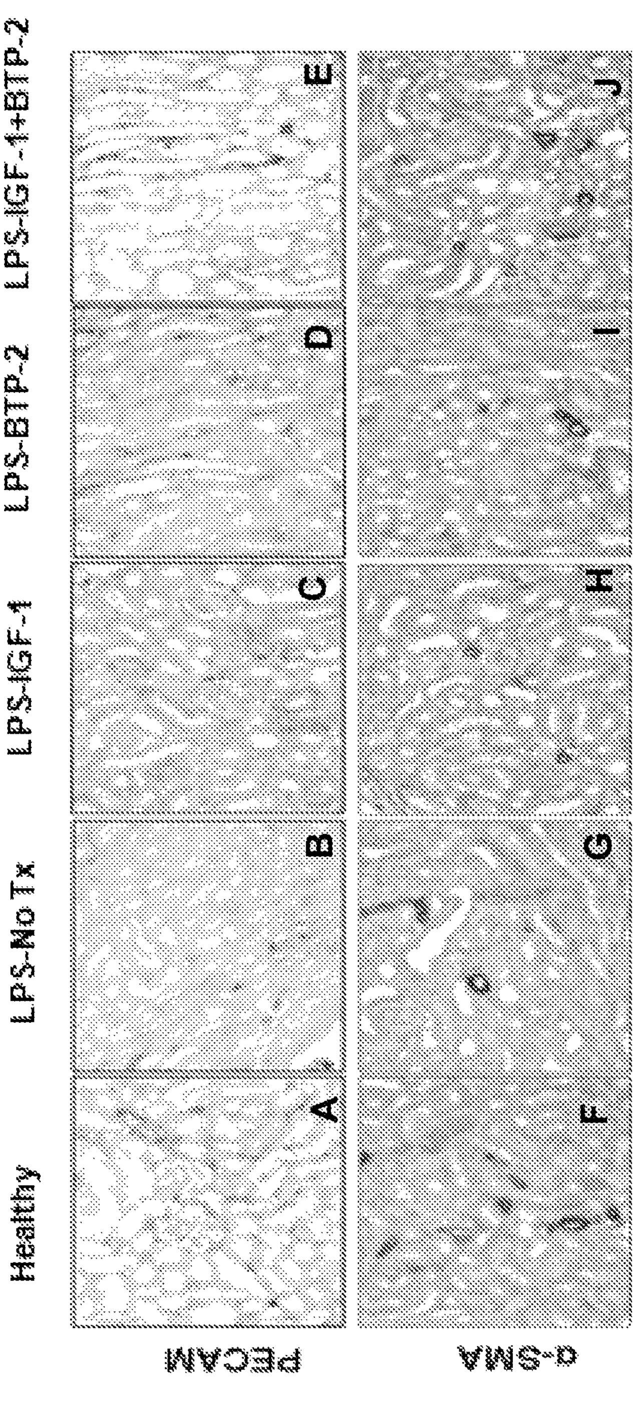
FIGS. 4A-4J are photographical representations of PECAM (CD-31) and α-SMA staining of healthy controls, and LPS-treated animals following no treatment and treatment with different components of the treatment regimen, individually and in combination.

One of the adverse effects of excess pro-inflammatory cytokine is vascular leakage. FIGS. 4A-4J are photographical representations of PECAM (CD-31) and α-SMA staining of healthy controls, and LPS-treated animals following no treatment and treatment with different components of the treatment regimen, individually and in combination. LPS administration caused a marked decrease in PECAM (CD-31) staining (FIGS. 4A and 4B), a change which was improved by IGF-I therapy (FIG. 4C) and also by BTP-2 therapy (FIG. 4D). In the combination therapy group (FIG. 4E), staining was improved over single therapy results but perhaps slightly decreased from normal. Similarly, LPS administration causes a decrease in α-SMA staining (FIGS. 4F and 4G), a change which was improved but IGF-I therapy (FIG. 411) and also by BTP-2 therapy (FIG. 4I). In the combination therapy group (FIG. 4J), the staining was improved over single therapy groups and appeared to be equivalent to normal. Both PECAM (CD-31) and α-SMA staining are parameters related to vascular integrity. Therefore, these results show substantial improvements with therapy in vascular gene expression and vascular staining parameters, but a substantial residual impairment in vascular leakage (FIGS. 4A-4J).

Figure 5A:
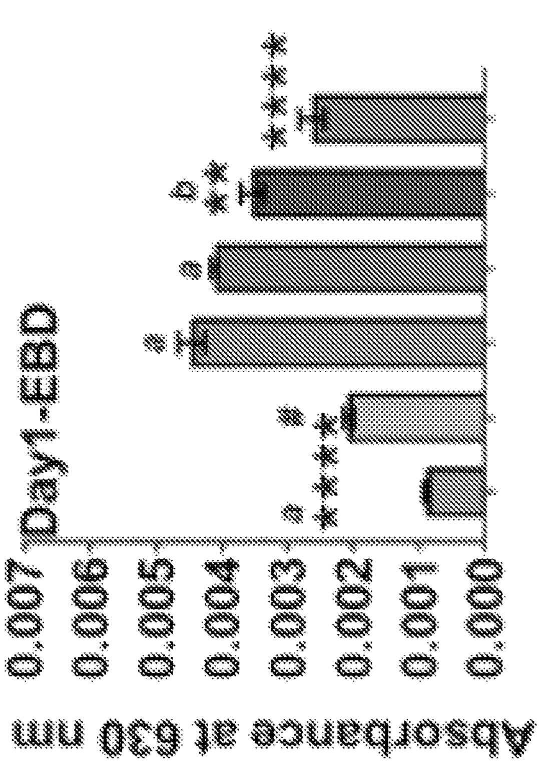
FIGS. 5A-5B are graphical representations of the extravasation of Evans blue dye for vascular leakage at day-1 and day-5 in healthy controls, and LPS-treated animals following no treatment and treatment with different components of the treatment regimen, individually and in combination.
Figure 5B:
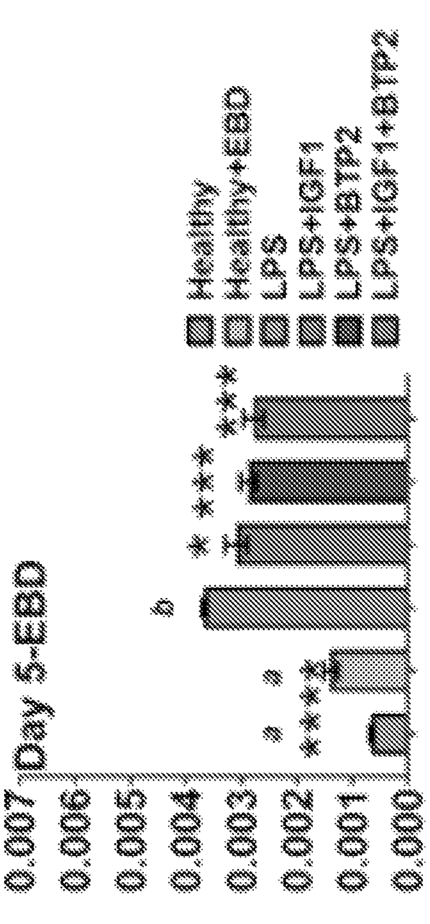

Because vascular leakage is a serious consequent of systemic AKI, the extravasation of Evans blue dye was examined for vascular leakage at day-1 and day-5 (FIGS. 5A and 5B). FIGS. 5A-5B are graphical representations of the extravasation of Evans blue dye for vascular leakage at day-1 and day-5 in healthy controls, and LPS-treated animals following no treatment and treatment with different components of the treatment regimen, individually and in combination. LPS treatment induced a marked increase in vascular leakage, which was improved by IGF-I and more so by BTP-2 treatment; whereas, both agents showed a more significant reduction than either one alone at the day 1-time point. Importantly, the 5-day time point (FIG. 5B) also showed significant decreases and leakage by both agents alone and together.

Figure 5C:
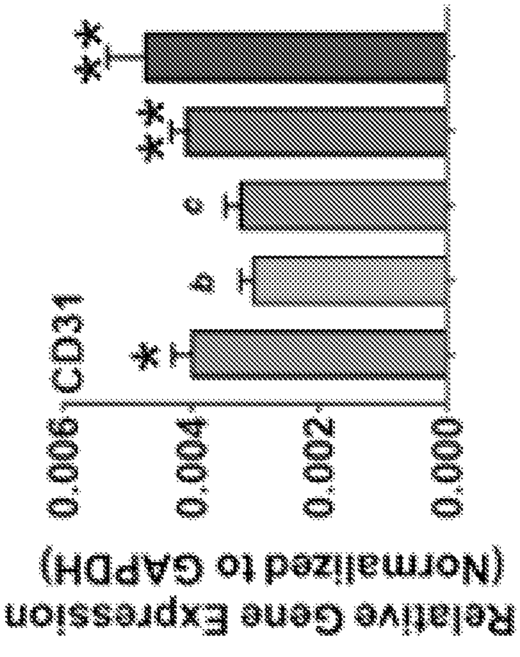
FIGS. 5C-5E are graphical representations of the relative gene expression of CD31, VEGF, and vascular endothelial Cadherin (VE-Cadherin), respectively, in healthy controls, and LPS-treated animals following no treatment and treatment with different components of the treatment regimen, individually and in combination. Data are mean±SEM*p<0.05,  p<0.01, * p<0.001, **** p<0.0001 (* LPS Vs other groups) and d-p<0.05, c-p<0.01, b-p<0.001, α-p<0.0001 (LPS+IGF1+BTP-2 Vs other groups), 1-way ANOVA followed by a Dunnett's multiple comparisons test, (n=4 in each group).
Figure 5D:
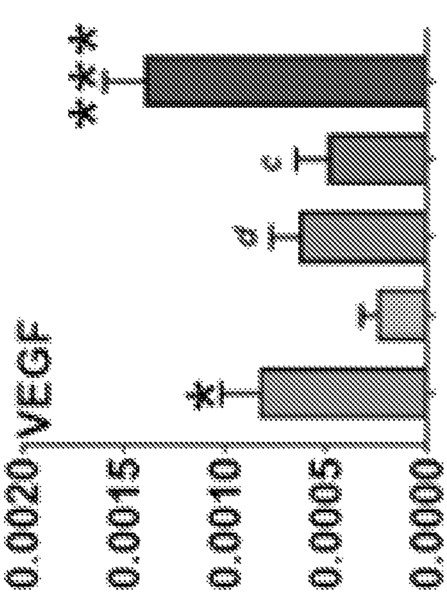

Importantly, the 5-day time point also showed significant decreases in leakage by the two agents together, but the results were not any more favorable than those seen at the day-1 time point. However, gene expression of CD31 (endothelial cell adhesion molecules, (PECAM-1), (FIG. 5C) was depressed by LPS and increased by BTP-2 and the combination therapy. FIGS. 5C-3E are graphical representations of the relative gene expression of CD31, VEGF, and vascular endothelial Cadherin (VE-Cadherin), respectively, in healthy controls, and LPS-treated animals following no treatment and treatment with different components of the treatment regimen, individually and in combination. Consistent with the gene expression data was the finding by immunocytochemistry of an increase in CD31 staining in the sections from the combination therapy animals compared to the LPS group (FIG. 5C). Additionally, the VEGF expression was synergistically increased above normal in the dual therapy, suggestive of continuing repair (FIG. 5D). The marked decrease in the expression of P16, a tumor suppressor gene, is also consistent with increased cell proliferation (but it could reflect changes not necessarily in endothelial cells since the samples contain renal tubular cells and immune cells). The difference in the effect of the combination treatment regimen in the Evan's blue dye leakage test as compared to the gene expression study is due to the fact that the leakage study was done in 5 days' post LPS administration versus the gene expression study that was done at 7 days' post LPS administration.

Renal Tubular Injury/Repair

Figure 6A:
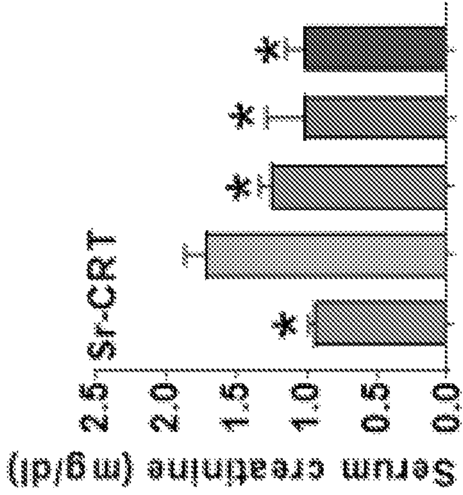
FIGS. 6A-6D are graphical representations of serum creatinine and the relative gene expression of molecules reflecting kidney damage-collagen type-1, NGAL, and Kim-1, respectively, in healthy controls, and LPS-treated animals following no treatment and treatment with different components of the treatment regimen, individually and in combination. Data are mean±SEM*p<0.05,  p<0.01, * p<0.001, **** p<0.0001 (* LPS Vs other groups) and d-p<0.05, c-p<0.01, b-p<0.001, α-p<0.0001 (LPS+IGF1+BTP-2 Vs other groups)), 1-way ANOVA followed by a Dunnett's multiple comparisons test, (n=4 in each group).
Figure 6A:
Figure 6B:
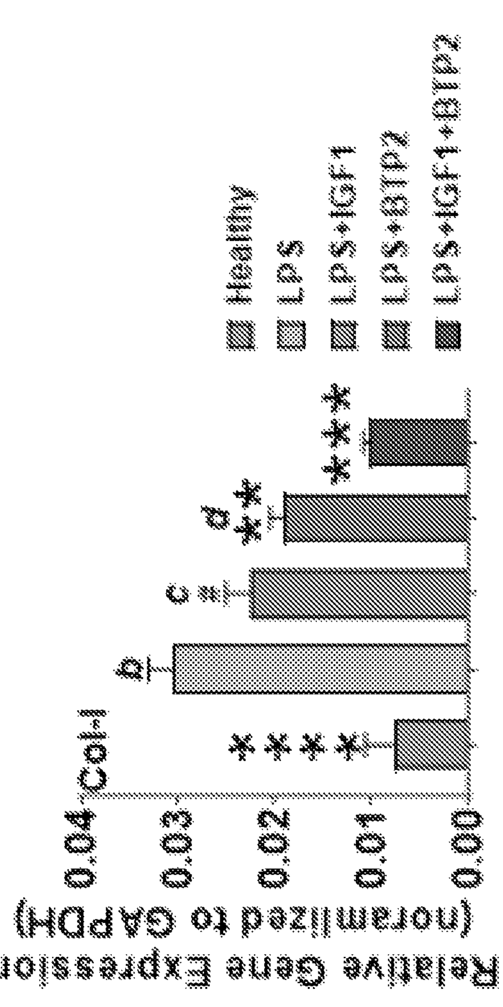
Figure 6B:
Figure 6C:
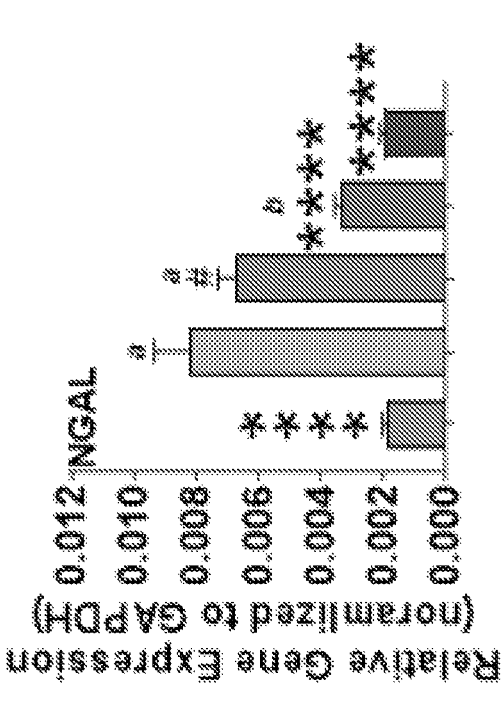
Figure 6D:
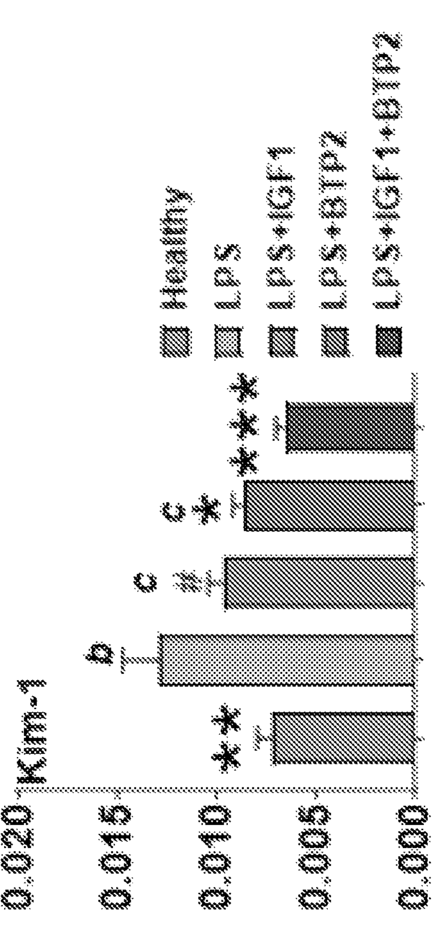
Figure 6D:

FIGS. 6A-6D are graphical representations of serum creatinine and the relative gene expression of collagen type-1, NGAL, and Kim-1, respectively, in healthy controls, and LPS-treated animals following no treatment and treatment with different components of the treatment regimen, individually and in combination. LPS treatment induced a large increase in serum creatinine, which was improved by IGF-I and normalized by the combination therapy and by BTP-2 at 48 hours (FIG. 6A). NGAL expression, which is more specific for renal function than serum creatinine, was markedly increased by LPS and improved by IGF-I and BTP-2 and by the combination therapy (FIG. 6C). Similarly, Kim-1 gene expression was improved by single therapies and normalized by combination therapy (FIG. 6D). Importantly, Kim-1 elevation is thought to reflect an increased risk of the development of maladaptive repair and interstitial fibrosis. Kim-1 was normal at the 7-day time point, suggesting that this therapy might help to reduce the risk of ultimate maladaptation repair. Also, at 7 days the expression of collagen type-1, a marker for tissue fibrosis, was markedly increased by LPS but normalized by combination therapy (FIG. 6B). The dual therapy decreases the risk of maladaptive repair.

Kidney Histopathology

Figures 7A, 7B, 7C, 7D, 7E, 7F, 7G, 7H, 7I, 7J:
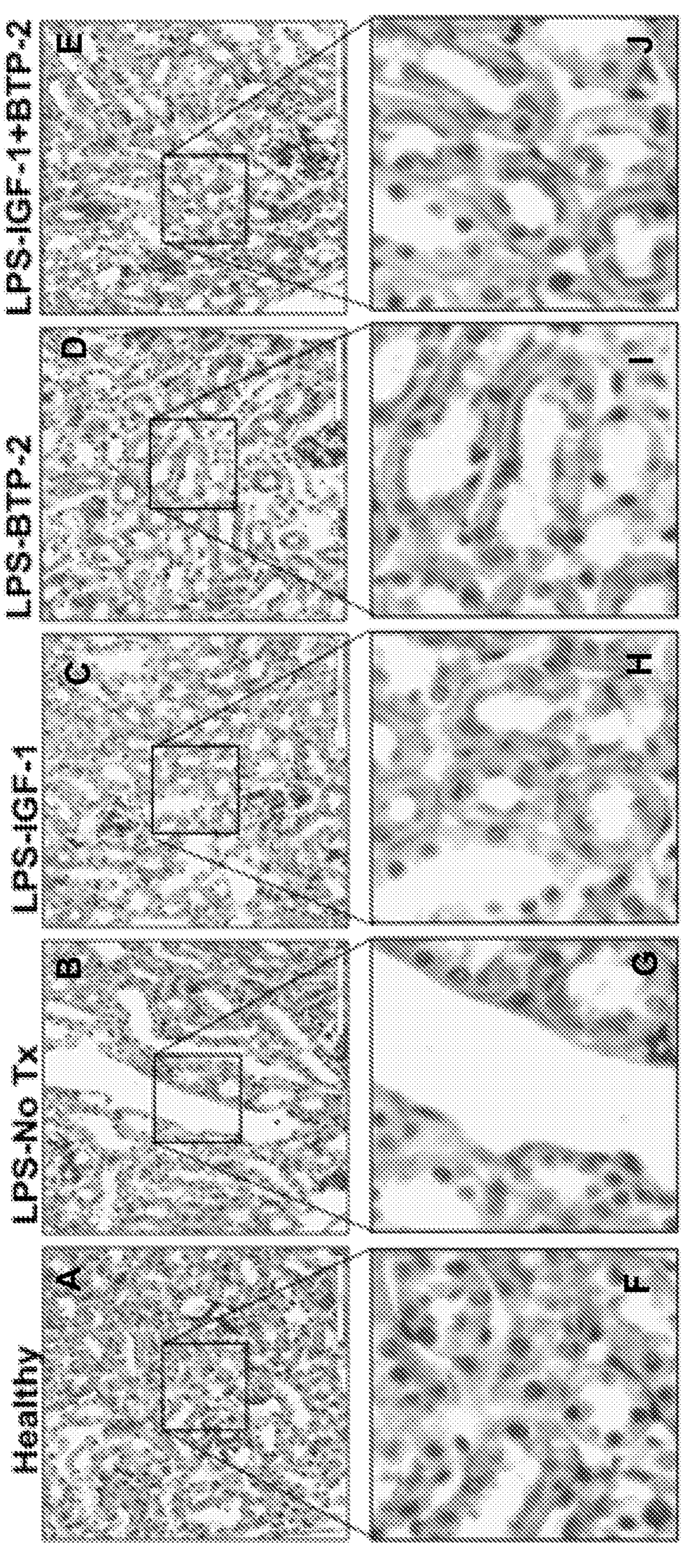
FIGS. 7A-7J are photographical representations of PAS staining on day 7 of kidney injury in healthy controls, and LPS-treated animals following no treatment and treatment with different components of the treatment regimen, individually and in combination (original magnification 40×; Scale bar, 100 μm).
Figures 7K, 7L:
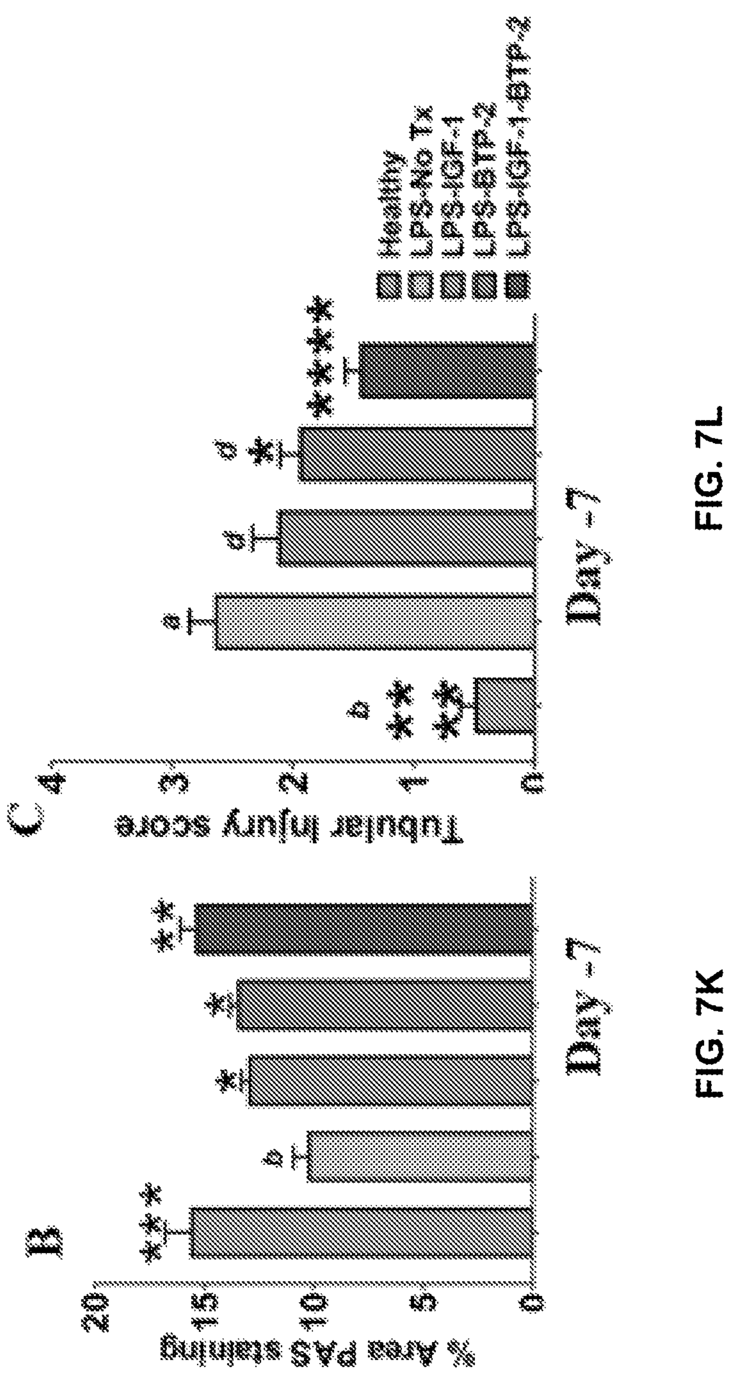
FIGS. 7K-7L are graphical representations of % Area of PAS staining and acute tubular injury score of mouse kidneys on day 7 of kidney injury in healthy controls, and LPS-treated animals following no treatment and treatment with different components of the treatment regimen, individually and in combination.

Quantitative measurements of PAS staining of the kidney tubule brush border showed a decrease in the LPS group and significant improvements by single therapy and normalization by combination therapy (FIGS. 7A-7J). The tubular injury score (FIG. 7K) was consistent with the results of PAS staining. There was a marked increase in the score in the LPS group and decreases in the score in single therapies and, particularly, the combination therapy. However, in contrast to the PAS staining, which was normalized in the combination therapy group, the tubular injury score was still elevated above the healthy group. Therefore, despite the normalization of AKI injury gene expression and PAS staining, there was statistically significant evidence of residual renal damage by the histopathology score (FIGS. 7K and 7L).

LPS administration caused a marked decrease in PECAM (CD-31) staining, a change which was improved by IGF-I therapy and also by BTP-2 therapy. In the combination therapy group, staining was improved over single therapy results but perhaps slightly decreased from normal. Similarly, LPS administration causes a decrease in α-SMA staining, a change which was improved by IGF-I therapy and also by BTP-2 therapy. In the combination therapy group, the staining was improved over single therapy groups and appeared to be equivalent to normal. Both PECAM (CD-31) and α-SMA staining are parameters related to vascular integrity. Therefore, substantial improvements were shown with therapy in vascular gene expression and vascular staining parameters, but a substantial residual impairment in vascular leakage. The combination therapy of BTP-2+IGF-I caused a 57% survival to a lethal dose of LPS and that the combination therapy was significantly better than either monotherapy compared to the LPS untreated group.

Figure 8:
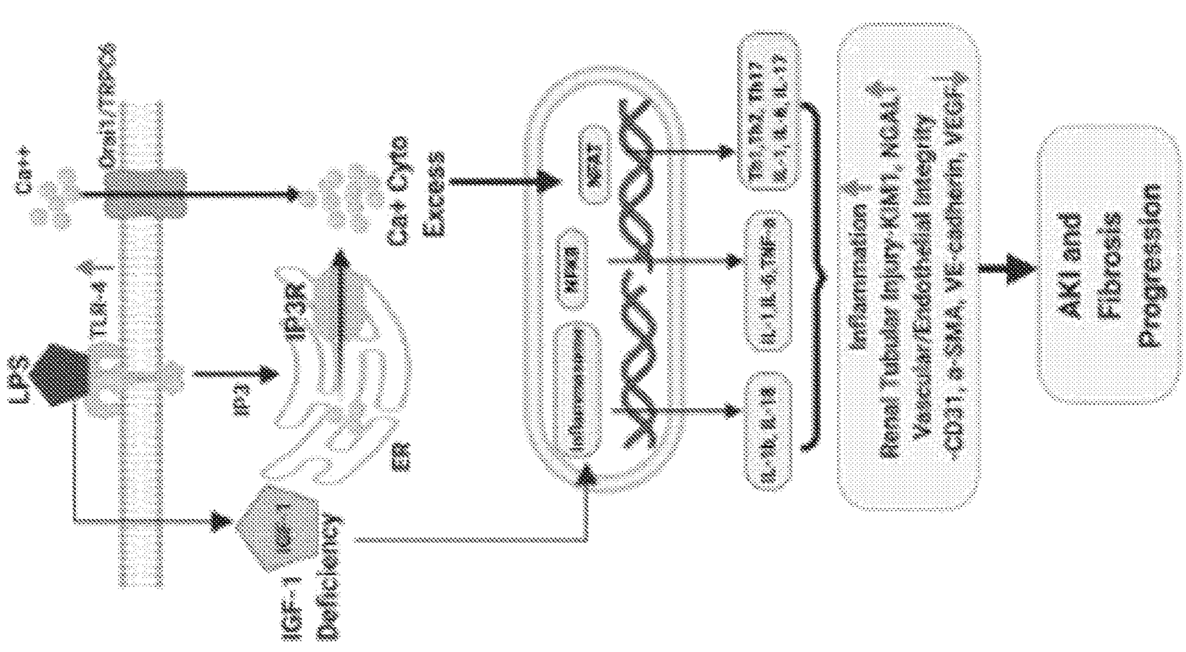
FIG. 8 is an illustration of the molecular pathway responses to the induction of AKI by LPS.
Figure 9:
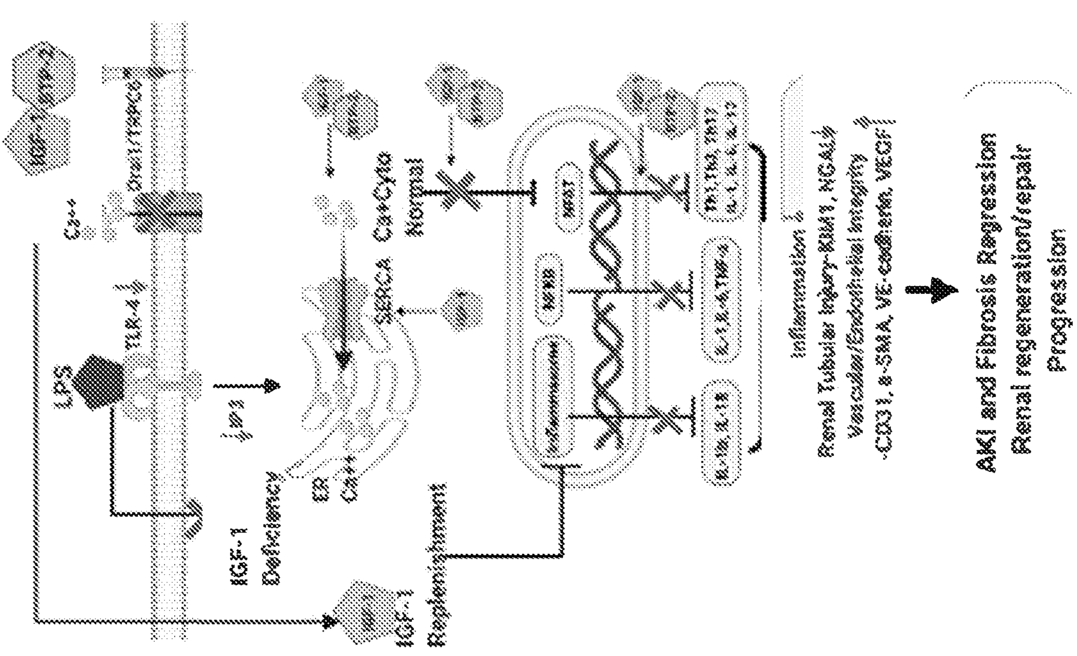
FIG. 9 is an illustration of the molecular pathway effects of combination therapy, IGF-I+BTP-2 to the induction of AKI by LPS.

Regarding mechanisms, the TLR-4 gene was markedly increased by LPS treatment and normalized in 7-days by IGF-1+BTP-2 combination therapy. One of the most fundamental actions of TLR-4 activation is to increase cytosolic calcium. TLR-4 activity increases the synthesis of pro-inflammatory cytokines in various cells at the site of inflammation, which in excess could have a negative impact on renal tubular function directly and through the corresponding decrease in vascular integrity. FIG. 8 is an illustration of the molecular pathway responses to the induction of AKI by LPS. FIG. 9 is an illustration of the molecular pathway effects of combination therapy, IGF-I+BTP-2 to the induction of AKI by LPS. These models facilitate an understanding of the therapeutic actions of the dual therapy. An early effect of LPS was chosen—an increase in IP3 receptor-induced calcium release from the ER into the cytosol, which is an established effect in LPS on lung microcapillaries. The next step is an increase in one or more STIM analogs, which occurs in response to the depletion of calcium from the ER stores. STIM activates Orai1, which is the core of the CRAC calcium channel that provides for calcium entry across the plasma membrane following depletion of the ER calcium store. Similarly, STIM may also activate TRPC6, which occurs in response to LPS that also increases cytosolic calcium through influx across the plasma membrane. No change in STIM-1 expression was detected, though this does not discount the potential that one of the other STIM analogs were upregulated or a specific cell type has to be evaluated, rather a heterogeneous populations of kidney cells. It is quite possible that by 7 days any increment in STIM-1 had become normal in response to therapy. An increase in Orai1 was detected in response to LPS and marked decrease in response to BTP-2 therapy. This decrease in Orai1 occurred 7 days after a single administration of BTP-2, raising the possibility of a prolonged biological half-life. Although cytosolic calcium was not measured in these studies, an increase in Nfat in response to LPS strongly supports the finding that there was a sustained increase in cytosolic calcium. BTP-2 decreases calcium influx into the cytosol by both TrpC6 and the CRAC channels. There is an additional potential mechanism involved in the reduction of cytosolic calcium by the treatment regimen of IGF-I and a CRAC channel inhibitor.

With respect to the effect of LPS to promote ER calcium release into the cytoplasm, IGF-I is known to stimulate SERCA in muscle tissue, which is in ATPase functioning to transport calcium from the cytosol into the ER. As illustrated in FIGS. 8 and 9, it would indicate that not only BTP-2 but also IGF-I also acts to decrease elevated cytosolic calcium caused by LPS administration. Orai1 positive cells have been shown to be responsible for the chronic maladaption action to AKI that eventually leads to interstitial fibrosis and chronic renal disease. In this regard, treatment regimen of IGF-I and a CRAC channel inhibitor decreased expression of Orai1 to below the normal level and this was associated with a rescue of the increase in type I collagen renal tissue at 7 days (FIGS. 2E and 6B).

Figure 5E:
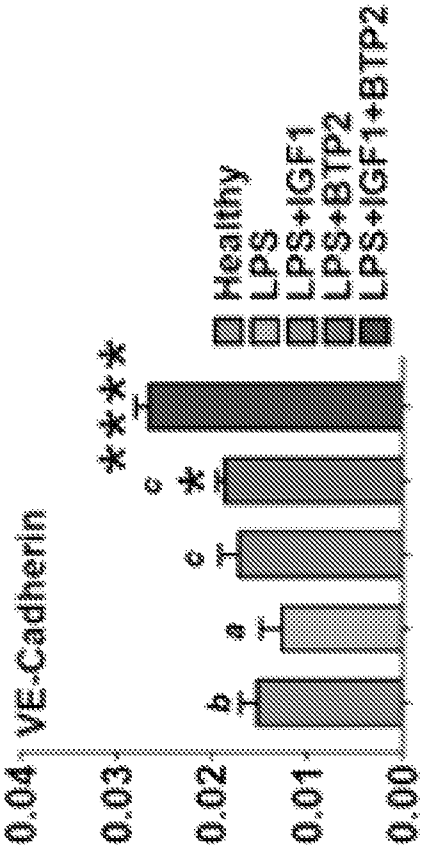

The only major process that was not substantially improved in 5 to 7 days of dual therapy was vascular integrity, as evidenced by vascular leakage, for which there were several potential applicable causes. Expression of pro-inflammatory cytokines, such IL-1 and TNF-α, were increased, which can lead to vascular leakage (FIGS. 3A-3E). LPS induces an increase in cytosolic calcium, which leads to an increase in PKC-α, which in turn dissembles VE-Cadherin, a major endothelial adhesion molecule. A marked decrease in expression of VE-Cadherin (FIG. 5E) with LPS treatment and favorable overcorrection with the combination therapy was observed. The overcorrection suggests that the process of vascular repair was not complete. LPS decreased α-SMA expression (which is a marker for Pericytes) and the combination therapy improved α-SMA staining as determined by immunocytochemistry. A loss of pericytes is associated with vascular leakage. Decreased 125-dihydroxy vitamin D synthesis (the barrier hormone), could have occurred because it requires adequate IGF-I levels and because IGF-I is clearly decreased in response to sepsis and inflammation due to AKI (FIG. 1A). The combination therapy increased VEGF expression above normal in the kidney (FIG. 5D). The increase in VEGF was a compensatory effort to repair the vascular injury. However, it is noteworthy that VEGF alone can cause vascular leakage apparently by causing the formation of new capillaries, which typically exhibit increased permeability. This raises the possibility that increasing the length of the therapy would afford further improvements. IGF-I treatment is also a potential mechanism for the increase in VEGF gene expression. Because the impairment in vascular permeability at 7 days was greater than the architectural abnormality of histologic tubular injury, perhaps the defect in vascular integrity in response to LPS after 7 days of combination treatment is due to both architectural as well as functional vascular impairment.

With respect to tubular cell injury, LPS caused marked increases in both NGAL and Kim-1, which are markers of renal tubular cell injury. Importantly, our combination therapy normalized the increase in NGAL expression and markedly reduced Kim-1 expression. Despite these favorable changes in gene expression, the histology studies indicate that the injury score was higher than normal; although this score did considerably improve with combination therapy. Histologic studies indicate architectural abnormalities in renal tubules at 7 days. The combination of IGF-I and a CRAC channel inhibitor present a viable clinical therapy for AKI. Administering a therapeutically effective amount of IGF-I and a CRAC channel inhibitor can treat other acute inflammatory syndromes, such as acute pulmonary injury, sepsis, coronavirus infection, and major/trauma surgery.

Example 5

Intracellular Signaling Pathways in Lungs in LPS-Treated Animal Models

Figures 10A, 10B, 10C, 10D, 10E, 10F, 10G, 10H:
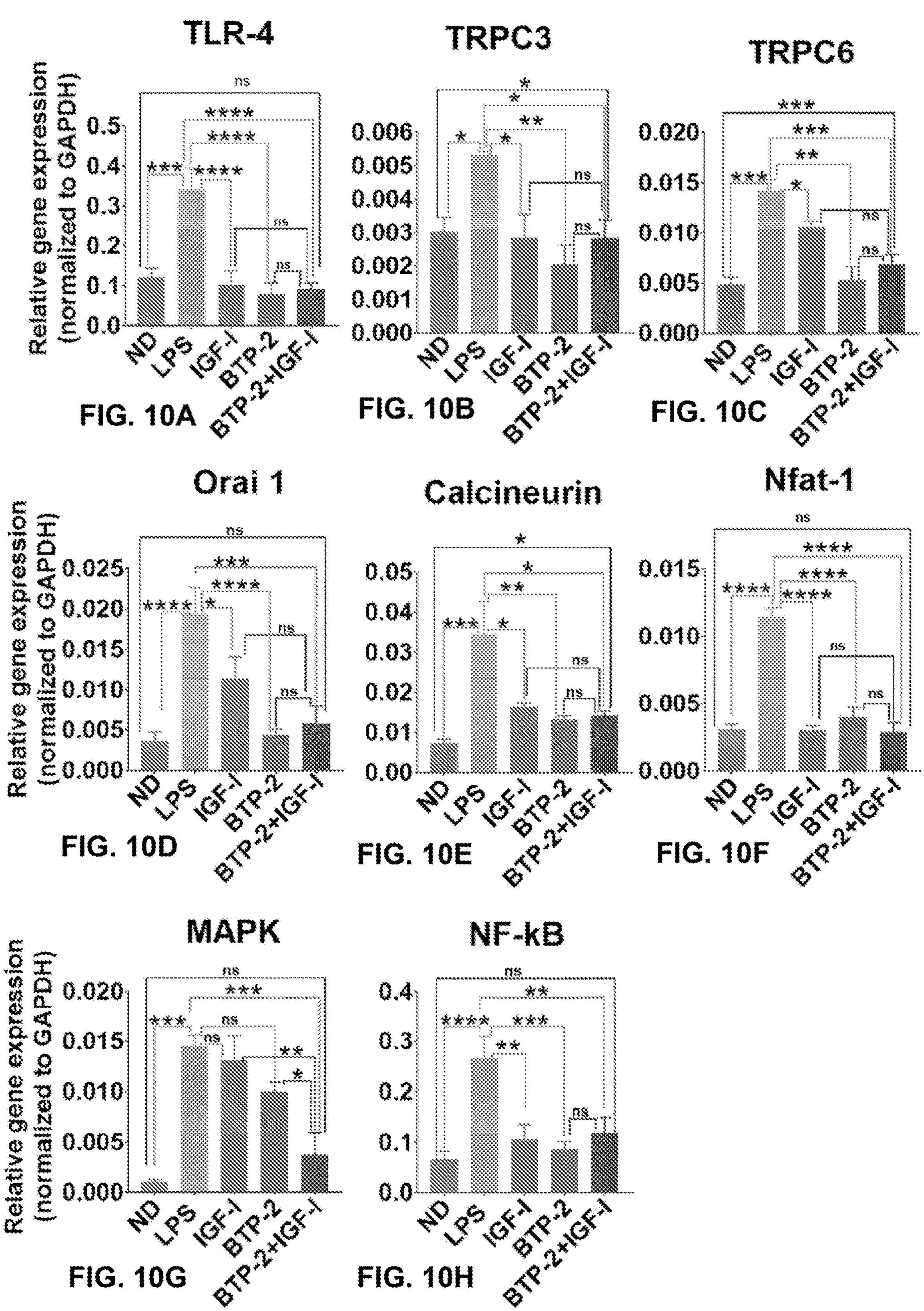
FIGS. 10A-10H are graphical representations of the relative mRNA expression of calcium channel regulators in the lungs of healthy controls, and LPS-treated animals following no treatment and treatment with IGF-1, BTP-2 monotherapies, and IGF-I+BTP-2 combination therapies.

A marked increase in the TLR-4 gene expression was found in the lungs seven days after LPS administration (FIG. 10A). IGF-I, BTP-2, or the combination therapy decreased the TLR-4 gene expression to the normal level. TLR-4 signaling reduces the calcium levels in the ER stores via the activation of inositol triphosphate (IP3) signaling, which, in turn, increases cytosolic calcium through the release of ER stores and the coordinated activation of the SOCE/CRAC channels. There was a significant decrease in Orai1 in the BTP-2 and combination therapy groups (FIG. 10D). The BTP-2 treatment also decreased the gene expression of calcineurin (FIG. 10E) and Nfat (FIG. 10F), reflecting a decrease in the cytosolic calcium. In this regard, the BTP-2 treatment also decreased TRPC3 (FIG. 10B) and TRPC6 (FIG. 10C), known to increase the plasma membrane calcium influx. BTP-2 inhibited the expression of Orai1 (FIG. 10D), TRPC3 (FIG. 10B), and TRPC6 (FIG. 10C) and led to a downstream decrease in calcineurin (FIG. 10E) and Nfat (FIG. 10F). Similar to the BTP-2 treatment, IGF-I treatment also decreased Orai1 (FIG. 10D), TRPC3 (FIG. 10B), and TRPC6 (FIG. 10C). The activation of TLR-4 (FIG. 10A) further induces the activation of the downstream signaling pathways, such as mitogen-activated protein kinase (MAPK) (FIG. 10G) and nuclear factor-kB (NF-kB) (FIG. 10H). A significant decrease in the gene expression of MAPK (FIG. 10G) and NF-kB (FIG. 10H) was demonstrated in the BTP-2 and IGF-I combination treatment group. FIGS. 10A-10H are graphical representations of the relative mRNA expression of calcium channel regulators in the lungs of healthy controls, and LPS-treated animals following no treatment and treatment with IGF-1, BTP-2 monotherapies, and IGF-I+BTP-2 combination therapies. FIGS. 10A-10H are graphical representations of the relative mRNA expression of TLR 4 (FIG. 10A), TRPC3 (FIG. 10A), TRPC6 (FIG. 10A), Orai1 (FIG. 10A), Calcineurin (FIG. 10A), NFAT-1 (FIG. 10A), MAPK (FIG. 10A) and, Nf-κB (FIG. 10A), respectively. Day 7 RT qPCR data are the mean±SEM. * $p<0.05$,  $p<0.01$, * $p<0.001$, and **** $p<0.0001$, ns-no significance. One-way ANOVA, followed by a Bonferroni's multiple comparisons test. Surprisingly, IGF-I affecting the plasma membrane calcium channels.

Inflammatory Cytokine Gene Expression in the Lungs

Figures 11A, 11B, 11C, 11D, 11E:
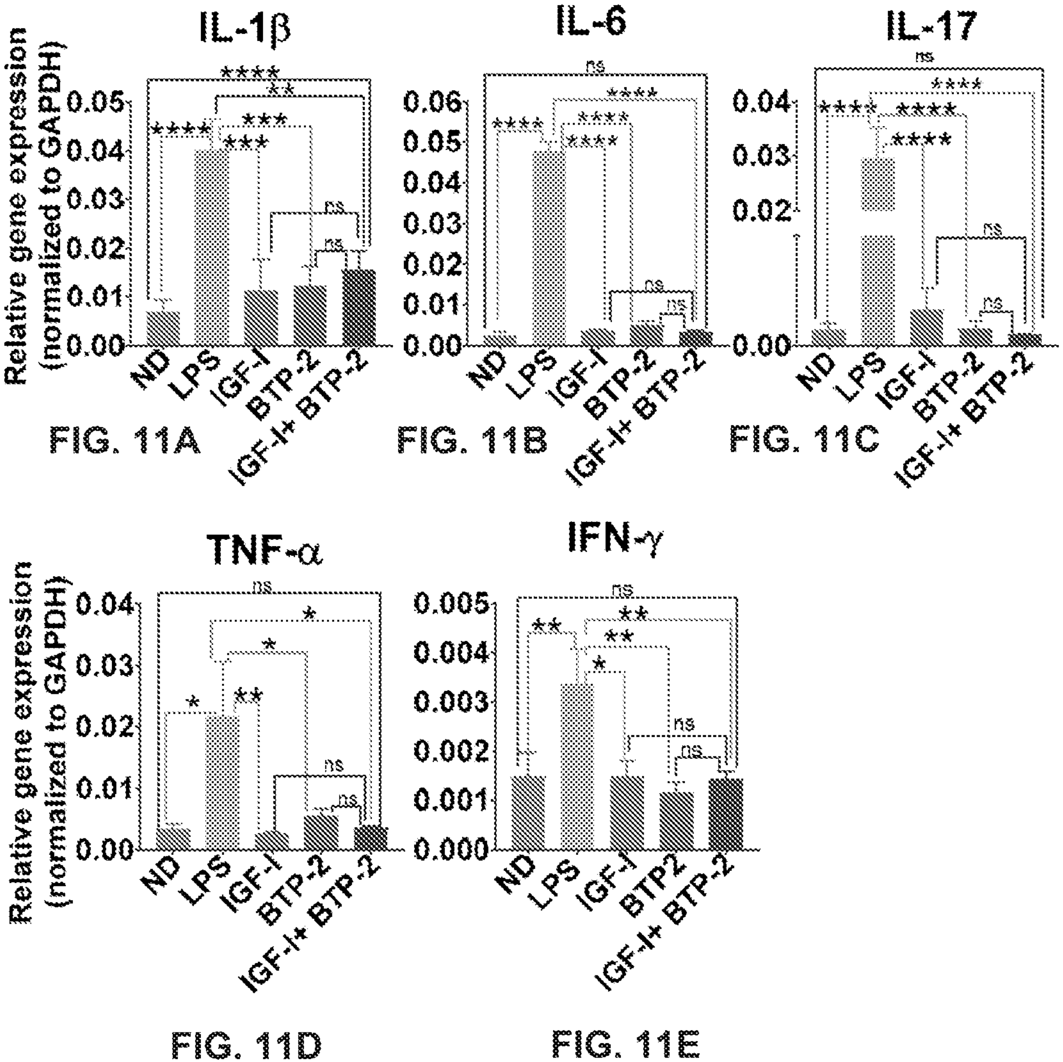
FIGS. 11A-11E are graphical representations of the relative mRNA expression of major proinflammatory cytokines in the lungs of healthy controls, and LPS-treated animals following no treatment and treatment with IGF-1, BTP-2 monotherapies, and IGF-I+BTP-2 combination therapies. Day 7 RT-qPCR of the markers IL-10 (FIG. 11A), IL-6 (FIG. 11B), IL-17 (FIG. 11C), TNF-α (FIG. 11D), and IFN-γ (FIG. 11E). Data are the mean±SEM. * p<0.05,  p<0.01, * p<0.001 and **** p<0.0001, ns-no significance. One-way ANOVA, followed by a Bonferroni's multiple comparisons test.

LPS administration caused a highly significant increase in the gene expression important proinflammatory cytokines IL-1p (FIG. 11A), IL-6 (FIG. 11B), IL-17 (FIG. 11C), IFN-γ (FIG. 11D), and TNF-α (FIG. 11E) after seven days of treatment. In sharp contrast, the treatment with IGF-I or BTP-2 or the combination therapy decreased the gene expression most of the proinflammatory cytokines to normal. FIGS. 11A-11E are graphical representations of the relative mRNA expression of major proinflammatory cytokines in the lungs of healthy controls, and LPS-treated animals following no treatment and treatment with IGF-1, BTP-2 monotherapies, and IGF-I+BTP-2 combination therapies. Day 7 RT-qPCR of the markers IL-10 (FIG. 11A), IL-6 (FIG. 11B), IL-17 (FIG. 11C), TNF-α (FIG. 11D), and IFN-γ (FIG. 11E). Data are the mean SEM. * $p<0.05$,  $p<0.01$, * $p<0.001$ and **** $p<0.0001$, ns-no significance. One-way ANOVA, followed by a Bonferroni's multiple comparisons test.

The above-observed effects of IGF-I or BTP-2, or the combination therapy, have important clinical implications. IL-1 is a proinflammatory cytokine produced by many cell types but, particularly, by activated macrophages and functions in general to promote cell proliferation and apoptosis. IL-6, produced by mesenchymal cells and immune cells, is a pleiotropic inflammatory cytokine responsible for acute protein synthesis and neutrophil migration in inflammatory sites. Importantly, IL-6 is also required for combating viral infections. IGF-I's effect to markedly decrease the IL-6 expression in inflammation has not been previously reported. Both IGF-I and BTP-2 markedly decreased the IL-17 expression. IL-17 is produced by CD4 T-helper cells and functions as the immune system's cytokine sentinel. IL-17 performs surveillance functions, maintenance of the mucosal barrier integrity, and recruitment of myeloid cells, increasing granulocyte colony stimulating factor (G-CSF). Both the IGF-I and BTP-2 treatments caused marked decreases in the expression of lung TNF-α, which is primarily produced by macrophages. TNF-α triggers the production of both IL-1 and IL-6. Significantly, TNF-α adversely affects endothelial adhesion molecules, resulting in vascular leakage. Interestingly, it is known that TNF-α downregulates the hepatic GHR expression, leading to a depression of circulating IGF-I during the inflammatory states. Although the LPS-model is one of sterile inflammation, in studies of infectious inflammation, TNF-α and IFN-γ are important proinflammatory cytokines known to create tissue damage. Interestingly, both cytokines' gene expressions were decreased by the treatment with IGF-I or BTP-2 or the combination therapy. With respect to the expression of IFN-γ, which the IGF-I and BTP-2 therapies corrected, it has been shown that IFN-γ-deficient mice are resistant to septic shock.

Vascular Integrity

Figures 12A, 12B, 12C:
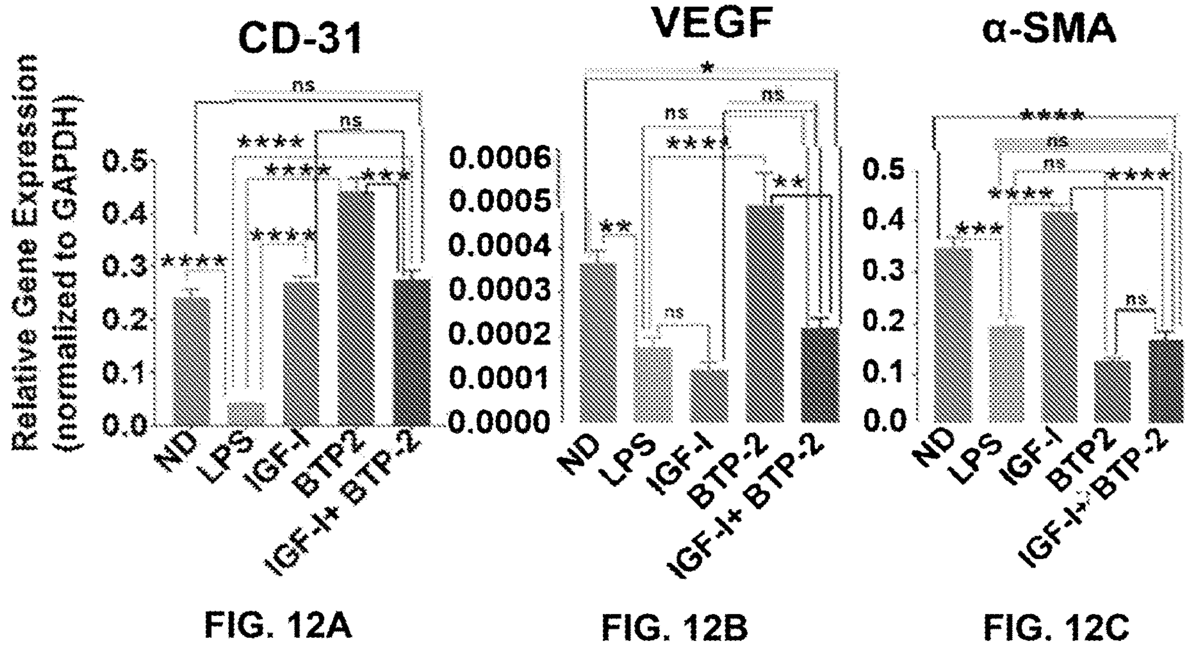
FIGS. 12A-12C are graphical representations of the relative mRNA expression of the vascular integrity markers CD31 (FIG. 12A), VEGF (FIG. 12B), and α-SMA (FIG. 12C) in the lungs of healthy controls, and LPS-treated animals following no treatment and treatment with IGF-1, BTP-2 monotherapies, and IGF-1+BTP-2 combination therapies. Data are the mean±SEM. * p<0.05,  p<0.01, * p<0.001, **** p<0.0001 and ns-no significance. One-way ANOVA, followed by Dunnett's multiple comparisons test.
Figures 13A, 13B, 13C, 13D, 13E, 13F, 13G, 13H, 13I, 13J:
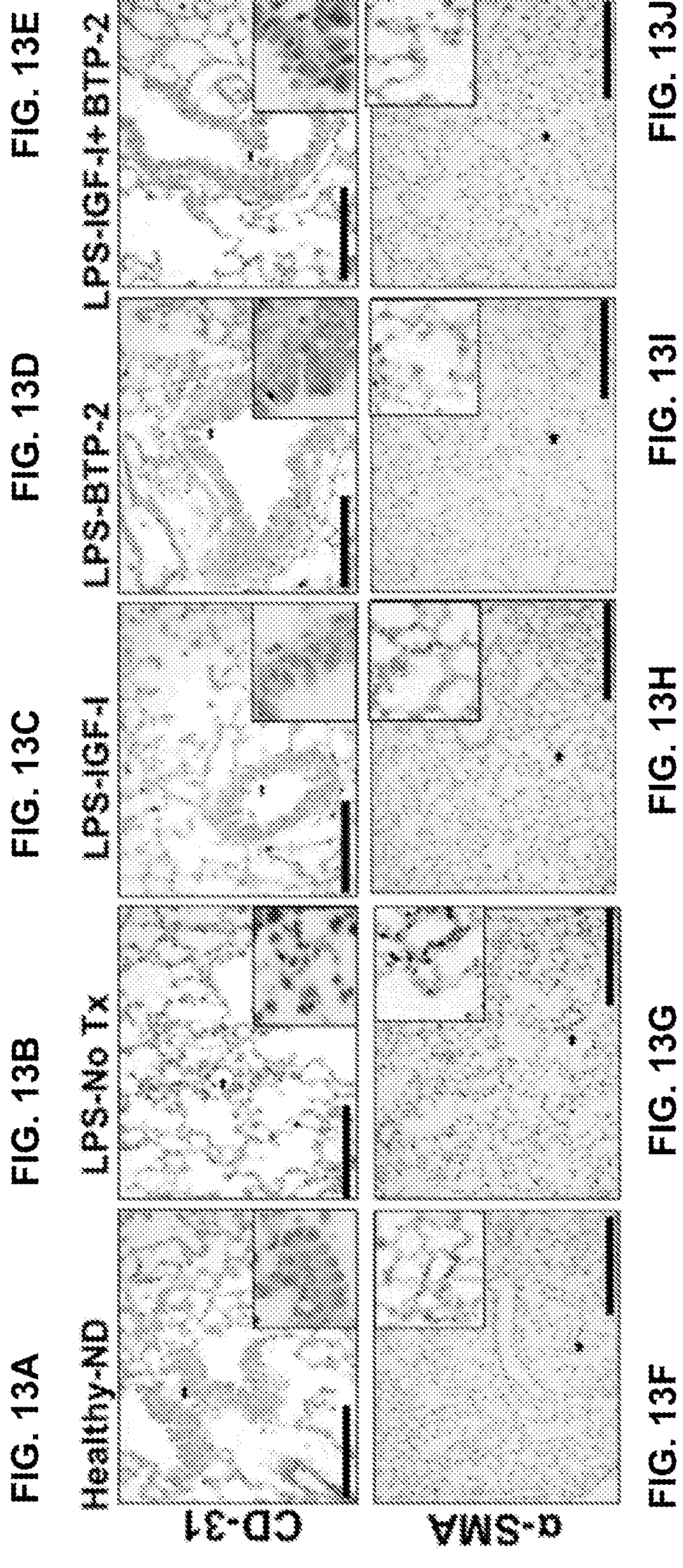
FIGS. 13A-13J are immunohistochemical (IHC) staining for CD31 and α-SMA in the lung sections of healthy controls, and LPS-treated animals following no treatment and treatment with IGF-1, BTP-2 monotherapies, and IGF-1+BTP-2 combination therapies. Data are the mean±SEM. * p<0.05,  p<0.01, * p<0.001, **** p<0.0001 and ns-no significance. One-way ANOVA, followed by Dunnett's multiple comparisons test. Scale: 200 μM.
Figure 14A:
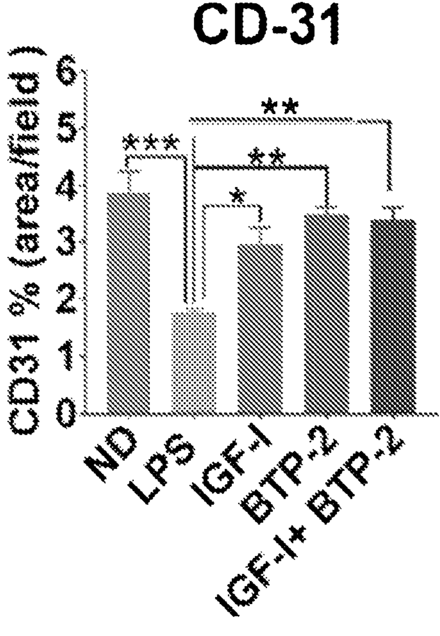
FIGS. 14A-14B are graphical representations of the IHC data in the form of a % of the area of CD31 staining (FIG. 14A) and the average number of α-SMA positive cells per field (FIG. 14B) in the lungs of healthy controls, and LPS-treated animals following no treatment and treatment with IGF-1, BTP-2 monotherapies, and IGF-1+BTP-2 combination therapies. Data are the mean SEM. * p<0.05,  p<0.01, * p<0.001, **** p<0.0001 and ns—no significance. One-way ANOVA, followed by Dunnett's multiple comparisons test.
Figure 14B:
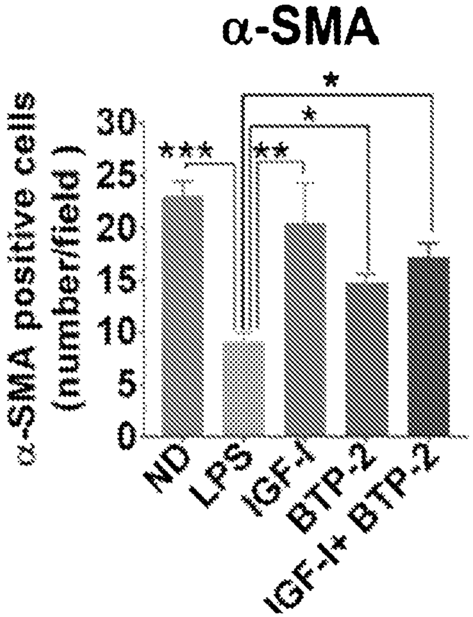

A quantitative gene expression analysis was done to measure the CD31 (platelet endothelial cell adhesion molecule-1 or PECAM-1), α-smooth muscle actin (α-SMA), and vascular endothelial growth factor (VEGF) expressions relevant to endothelial cells. FIGS. 12A-12C are graphical representations of the relative mRNA expression of the vascular integrity markers CD31 (FIG. 12A), VEGF (FIG. 12B), and α-SMA (FIG. 12C) in the lungs of healthy controls, and LPS-treated animals following no treatment and treatment with IGF-1, BTP-2 monotherapies, and IGF-1+BTP-2 combination therapies. Data are the mean±SEM. * $p<0.05$,  $p<0.01$, * $p<0.001$, ** $p<0.0001$ and ns-no significance. One-way ANOVA, followed by Dunnett's multiple comparisons test. FIGS. 13A-13**J are immunohistochemical (IHC) staining for CD31 and α-SMA in the lung sections of healthy controls, and LPS-treated animals following no treatment and treatment with IGF-1, BTP-2 monotherapies, and IGF-1+BTP-2 combination therapies. Data are the mean±SEM. * $p<0.05$,  $p<0.01$, * $p<0.001$,

** $p<0.0001$ and ns-no significance. One-way ANOVA, followed by Dunnett's multiple comparisons test. Scale: 200 μM. FIGS. 14A-14B are graphical representations of the IHC data in the form of a % of the area of CD31 staining (FIG. 14A) and the average number of α-SMA positive cells per field (FIG. 14**B) in the lungs of healthy controls, and LPS-treated animals following no treatment and treatment with IGF-1, BTP-2 monotherapies, and IGF-1+BTP-2 combination therapies. Data are the mean±SEM. * $p<0.05$,  $p<0.01$, * $p<0.001$, **** $p<0.0001$ and ns-no significance. One-way ANOVA, followed by Dunnett's multiple comparisons test.

LPS caused a significant decrease in the VEGF gene expression in the lungs (FIGS. 12A-12C, FIGS. 13A-13J, and FIGS. 14A-14B). BTP-2 therapy markedly increased the VEGF expression, whereas IGF-I did not affect the VEGF expression. The physiological significance of the VEGF expression changes is unclear, as VEGF is also associated with vascular leakage. Accordingly, VEGF expression changes could represent a repair process or a potential mechanism for the observed leakage. The IGF-I and BTP-2 combination therapy did not increase the VEGF expression, raising the possibility that IGF-I inhibited the effect of BTP-2 on the VEGF expression. CD31, another gene related to vascular integrity, was markedly decreased by LPS but corrected by BTP-2 and IGF-I therapy and the combination therapy (FIGS. 12A-12C, FIGS. 13A-13J, and FIGS. 14A-14B). The immunocytochemical evaluation of CD31 on the lung vasculature revealed that the amount of space occupied by endothelial cells was markedly reduced by LPS administration and significantly improved by IGF-I, BTP-2, or the combination therapy (FIGS. 12A-12C, FIGS. 13A-13J, and FIGS. 14A-14B). Thus, the gene expression of CD31 and the immunocytochemical evaluation of CD31-positive cells showed an improvement with all three therapeutic groups. Specific to the vasculature is α-SMA, a marker for smooth muscle actin, but it can be an index of pericyte activity. Pericytes are located at endothelial cell junctions and function to prevent vascular leakages. LPS caused a significant decrease in the α-SMA gene expression and α-SMA+ cells (FIGS. 12A-12C, FIGS. 13A-13J, and FIGS. 14A-14B). BTP-2 therapy completely corrected the LPS-induced reduction in α-SMA gene expression. Treatment with IGF-I did not indicate such beneficial effects. The combination therapy reflected the impact of BTP-2 rather than IGF-I. However, the immunohistochemistry analyses showed that all three therapeutic modalities ameliorated the LPS-induced decrease in the α-SMA+ cells (FIGS. 13A-13J).

Lung Tissue Damage and Repair

Figures 15A, 15B, 15C:
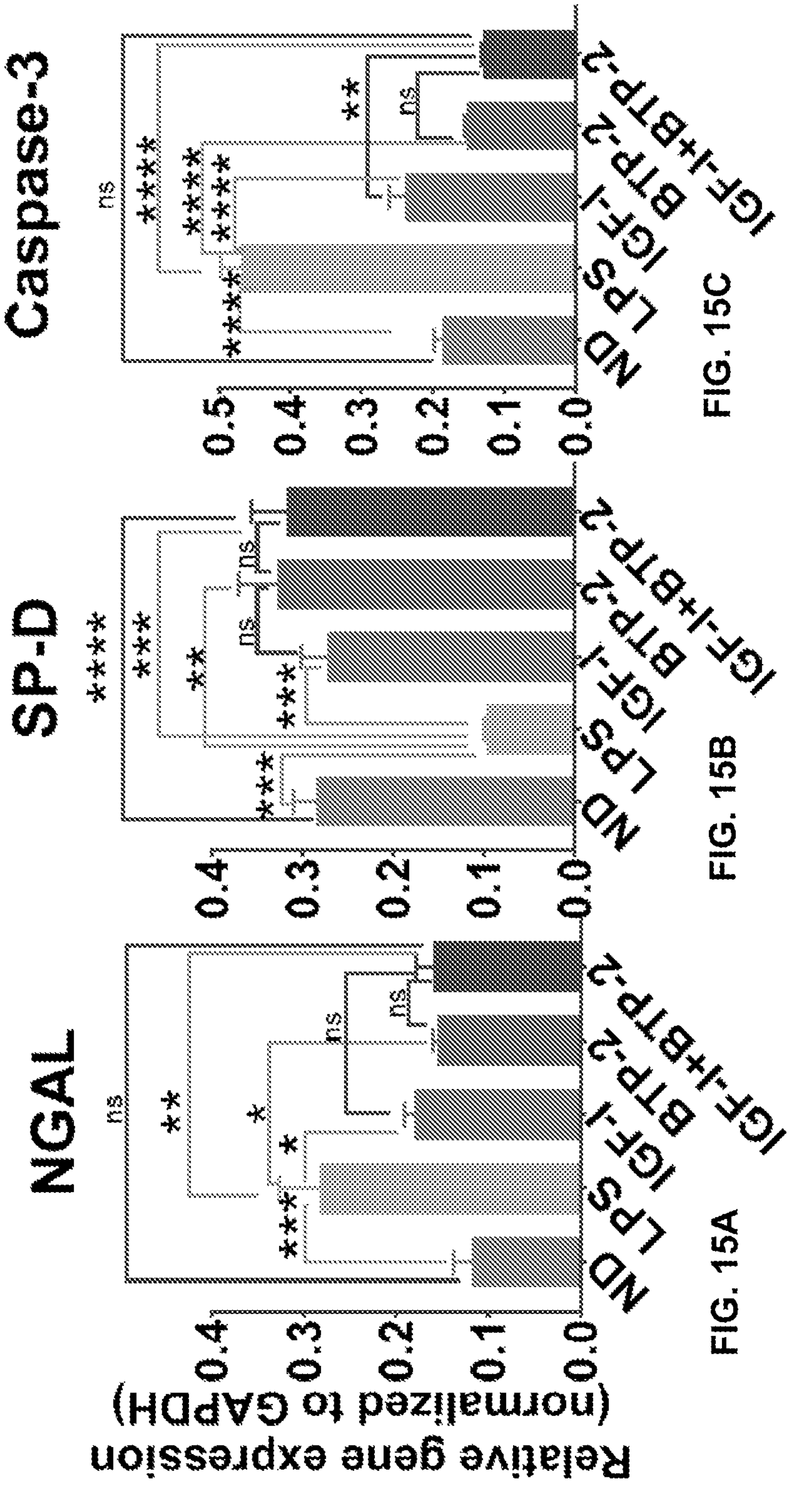
FIGS. 15A-15C are graphical representations of the injury and repair markers—NGAL (FIG. 15A), SP-D (FIG. 15B), and Caspase-3 (FIG. 15C)—in the lungs of healthy controls, and LPS-treated animals following no treatment and treatment with IGF-1, BTP-2 monotherapies, and IGF-1+BTP-2 combination therapies. Day 7 RT-qPCR for the injury markers NGAL and caspase-3 and repair marker SP-D. Data are the mean±SEM. * p<0.05,  p<0.01, * p<0.001, **** p<0.0001 and ns-no significance. One-way ANOVA, followed by Bonferroni's multiple comparisons test.
Figures 16A, 16B, 16C, 16D, 16E:
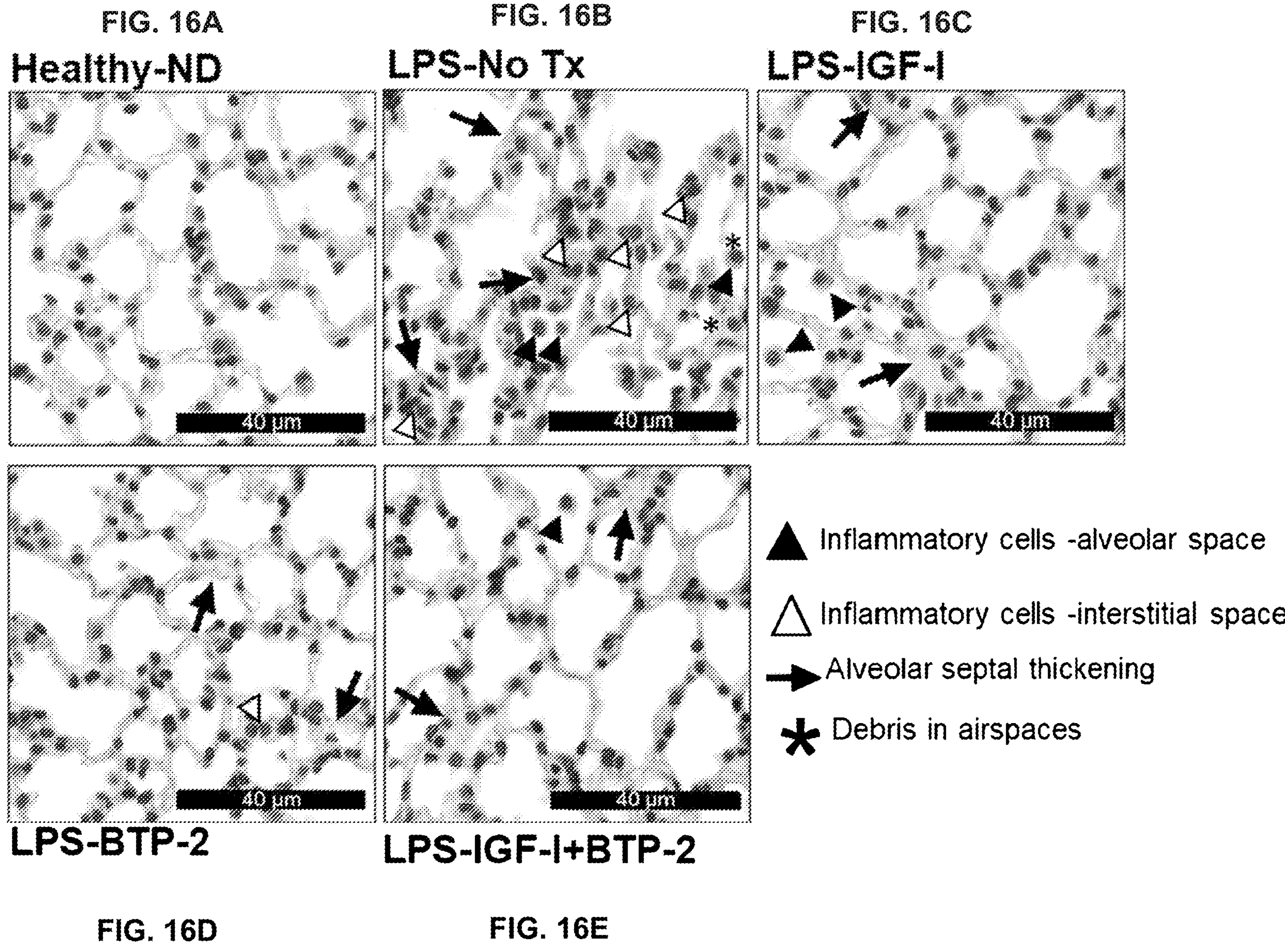
FIGS. 16A-16E are immunohistochemical (IHC) staining of the lung sections of healthy controls, and LPS-treated animals on Day 7 following no treatment and treatment with IGF-1, BTP-2 monotherapies, and IGF-1+BTP-2 combination therapies to evaluate the tissue structures, such as inflammatory cells in the alveolar and interstitial space, alveolar septal thickening, and debris in air spaces. Scale: 40 μM.

The synthesis of antimicrobial protein neutrophil gelatinase-associated lipocalin-2 (LCN2/NGAL) increases in bronchial epithelial cells in response to inflammation. The NGAL expression was significantly increased in the lungs in response to LPS (FIGS. 15A-15C). Both the IGF-I and BTP-2 therapies significantly reduced the elevated NGAL expression almost to normal, as did the combination therapy. Surfactant protein D (SP-D) is a marker of alveolar epithelial cell proliferation during acute lung injury. FIGS. 15A-15C are graphical representations of the injury and repair markers—NGAL (FIG. 15A), SP-D (FIG. 15B), and Caspase-3 (FIG. 15C)—in the lungs of healthy controls, and LPS-treated animals following no treatment and treatment with IGF-1, BTP-2 monotherapies, and IGF-1+BTP-2 combination therapies. Day 7 RT-qPCR for the injury markers NGAL and caspase-3 and repair marker SP-D. Data are the mean±SEM. * $p<0.05$,  $p<0.01$, * $p<0.001$, **** $p<0.0001$ and ns-no significance. One-way ANOVA, followed by Bonferroni's multiple comparisons test.

There was a marked decrease in SP-D in response to LPS. Both IGF-I and BTP-2 normalized the marked depression of SP-D in the lungs, as did the combination therapy. The LPS treatment markedly increased the expression of caspase 3. With respect to the treatments with either IGF-I or BTP-2, both types of therapies corrected the elevated caspase 3 expression produced by LPS, as did the combination therapy (FIGS. 15A-15C).

Quantitative Lung Histology

The epithelial injury gene expression studies with four quantitative histological analysis parameters of the lung injury. LPS, at seven days, showed a marked disruption of the lung epithelium, as is evident from the quantitative data below and a massive invasion of inflammatory immune cells (FIGS. 16A-17E and FIGS. 17A-17E). FIGS. 16A-16E are immunohistochemical (IHC) staining of the lung sections of healthy controls, and LPS-treated animals on Day 7 following no treatment and treatment with IGF-1, BTP-2 monotherapies, and IGF-1+BTP-2 combination therapies to evaluate the tissue structures, such as inflammatory cells in the alveolar and interstitial space, alveolar septal thickening, and debris in air spaces. Scale: 40 μM.

Mean linear intercept: An increase in the mean linear intercept indicates an abnormal increase in the airspace. The mean linear intercept is the free distance between the gas exchange surfaces in the acinar airway complex. The mean linear intercept was increased in the LPS group, indicating an abnormal increase in the airspace, leading to a reduced gas exchange. All three treatment modalities improved the mean linear intercept score (FIGS. 16A-16E and FIG. 17A).

Destructive index: The destructive index is a measure of the alveolar septal damage. The criteria are alveolar septal breaks or collapses and airspace enlargement. In the LPS group, there was septal thickening and leukocyte infiltration of the alveoli. Accordingly, the damage was markedly increased in the LPS group and improved in all three therapeutic modalities (FIGS. 16A-16E and FIG. 17B). LPS markedly increased the destructive index, whereas the other three therapies normalized this index.

Area disrupted: The area disrupted parameter is a measurement of the percentage of visible area damage. The damage was indicated by septal thickening and leukocyte infiltration in the alveoli. LPS-induced inflammation caused neutrophil-dependent emphysematous changes in the lung architecture and apoptosis. All three therapeutic modalities improved these changes (FIGS. 16A-16E and FIG. 17C).

Mean septal thickness: The septal thickness represents the blood-air barrier thickness, which increases with an injury. The treatment with LPS caused a significant increase in the mean septal thickness, whereas all three therapeutic modalities normalized this parameter FIGS. 16A-16E and (FIG. 17D).

Figures 17A, 17B, 17C, 17D, 17E:
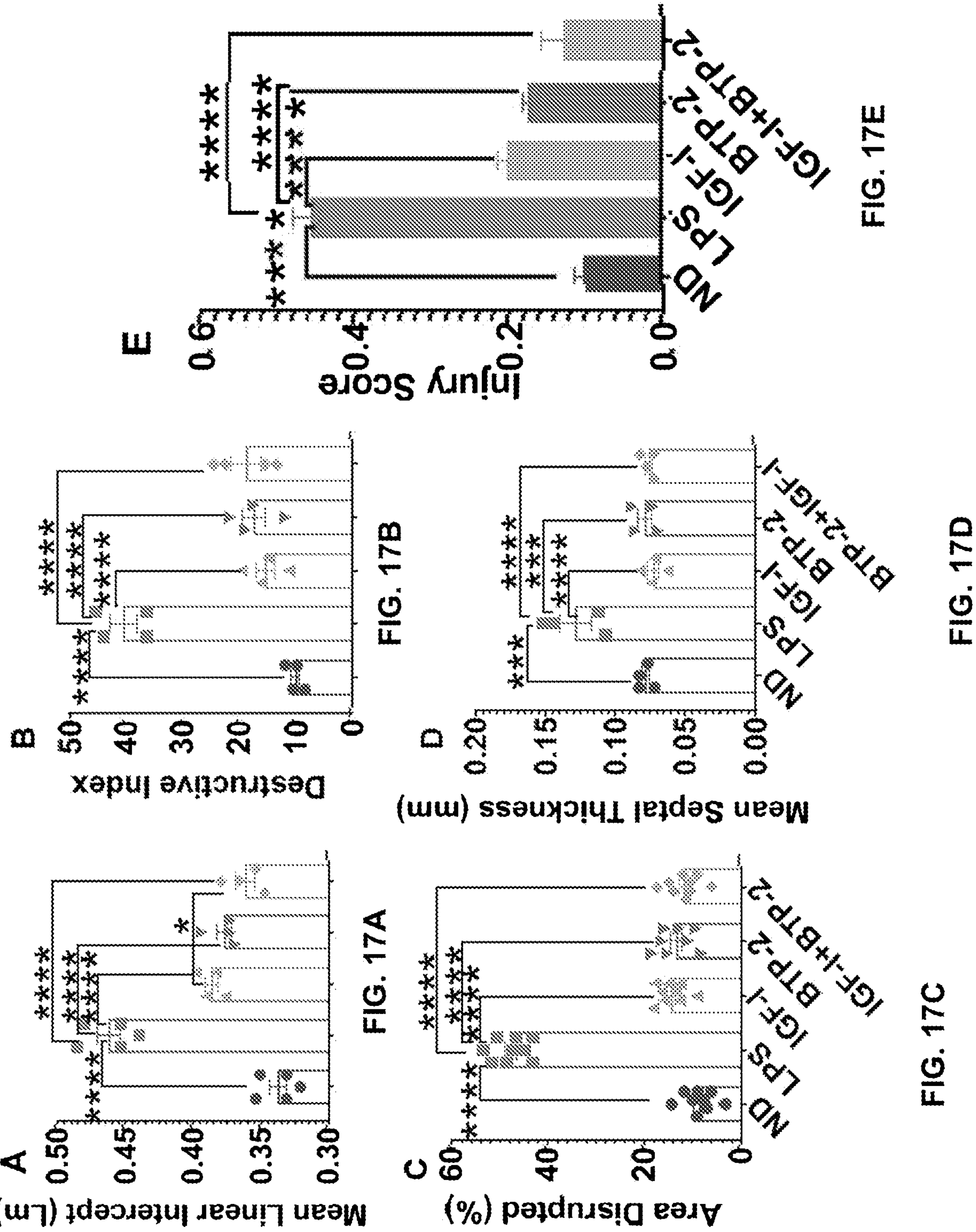
FIGS. 17A-17E are graphical representations of the histomorphometry parameters Mean linear intercept (FIG. 17A), destructive index (FIG. 17B), percentage of the area disrupted (FIG. 17C), mean septal thickness (FIG. 17D), and the injury score (FIG. 17E) were quantified by the evaluation on Day 7 of the lung sections stained by H&E of healthy controls, and LPS-treated animals following no treatment and treatment with IGF-1, BTP-2 monotherapies, and IGF-1+BTP-2 combination therapies. The histology quantification data are the mean±SEM. * p<0.05, * p<0.001, and ** p<0.0001. One-way ANOVA, followed by Dunnett's multiple comparisons test.
Figures 18A, 18B, 18C, 18D, 18E:
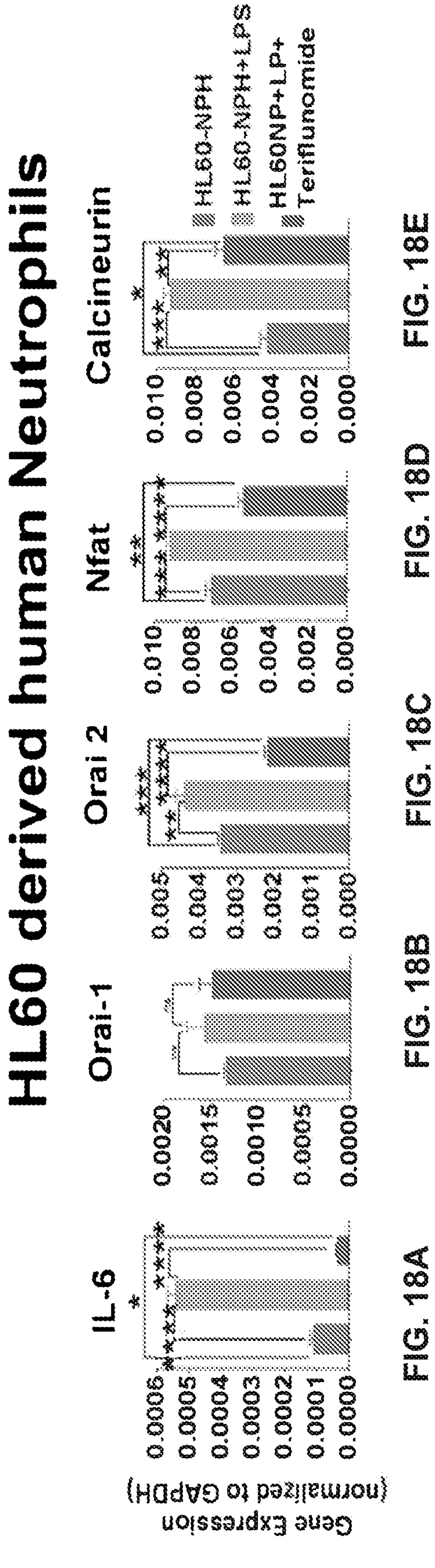
FIGS. 18A-18E are graphical representations of the relative mRNA expression of IL-6 (FIG. 18A), Orai-1 (FIG. 18B), Orai-2 (FIG. 18C), Nfat (FIG. 18D), and Calcineurin (FIG. 18E), respectively in HL60-derived human neutrophils, and those neutrophils subjected to treatment with LPS alone and then LPS-treated neutrophils following treatment with teriflunomide. Data are mean±SEM*p<0.05,  p<0.01, * p<0.001, **** p<0.0001. 1-way ANOVA followed by a Dunnett's multiple comparisons test.
Figures 19A, 19B, 19C, 19D, 19E:
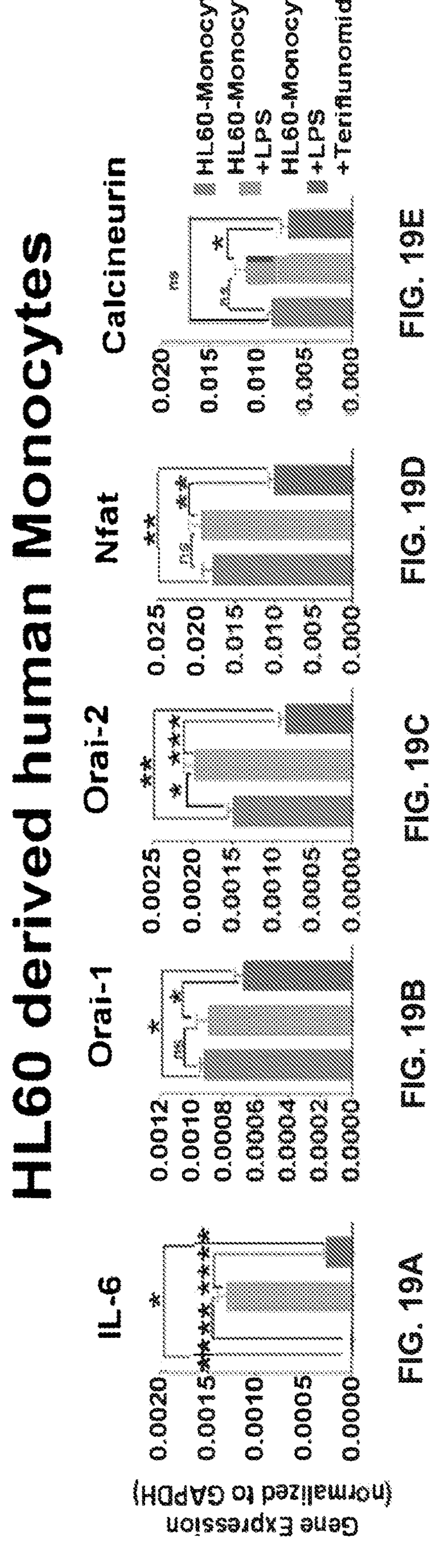
FIGS. 19A-19E are graphical representations of the relative mRNA expression of IL-6 (FIG. 19A), Orai-1 (FIG. 19B), Orai-2 (FIG. 19C), Nfat (FIG. 19D), and Calcineurin (FIG. 19E), respectively in HL60-derived human monocytes, and those monocytes subjected to treatment with LPS alone and then LPS-treated monocytes following treatment with teriflunomide. Data are mean±SEM*p<0.05,  p<0.01, * p<0.001, **** p<0.0001. 1-way ANOVA followed by a Dunnett's multiple comparisons test.

The four parameters were integrated into a total lung injury score, which showed that all the therapies, including the combination IGF-I+BTP-2 therapy, normalized the lung injury score (FIG. 17E). FIGS. 17A-17E are graphical representations of the histomorphometry parameters Mean linear intercept (FIG. 17A), destructive index (FIG. 17B), percentage of the area disrupted (FIG. 17C), mean septal thickness (FIG. 17D), and the injury score (FIG. 17E) were quantified by the evaluation on Day 7 of the lung sections stained by H&E of healthy controls, and LPS-treated animals following no treatment and treatment with IGF-1, BTP-2 monotherapies, and IGF-1+BTP-2 combination therapies. The histology quantification data are the mean±SEM. * $p<0.05$, * $p<0.001$, and ** $p<0.0001$. One-way ANOVA, followed by Dunnett's multiple comparisons test.

Example 6

Cytokine stimulation with LPS and treatment with teriflunomide was investigated using HL60-derived neutrophils and monocytes. These studies illustrate the robustness of the treatment with teriflunomide in human cells. As expected LPS increased IL-6, increased Orai 2, increased Nfat and increased calcineurin. All of these changes were significantly reduced by teriflunomide. This data demonstrates that teriflunomide counteracts the effect of LPS to increase cytosolic calcium, which in turn increases proinflammatory cytokines. FIGS. 18A-18E are graphical representations of the relative mRNA expression of IL-6 (FIG. 18A), Orai-1 (FIG. 18B), Orai-2 (FIG. 18C), Nfat (FIG. 18D), and Calcineurin (FIG. 18E), respectively in HL60-derived human neutrophils, and those neutrophils subjected to treatment with LPS alone and then LPS-treated neutrophils following treatment with teriflunomide. Data are mean±SEM*$p<0.05$,  $p<0.01$, * $p<0.001$, **** $p<0.0001$. 1-way ANOVA followed by a Dunnett's multiple comparisons test.

FIGS. 19A-19E are graphical representations of the relative mRNA expression of IL-6 (FIG. 19A), Orai-1 (FIG. 19B), Orai-2 (FIG. 19C), Nfat (FIG. 19D), and Calcineurin (FIG. 19E), respectively in HL60-derived human monocytes, and those monocytes subjected to treatment with LPS alone and then LPS-treated monocytes following treatment with teriflunomide. Data are mean±SEM*$p<0.05$,  $p<0.01$, * $p<0.001$, **** $p<0.0001$. 1-way ANOVA followed by a Dunnett's multiple comparisons test.

Example 7

Figure 20:
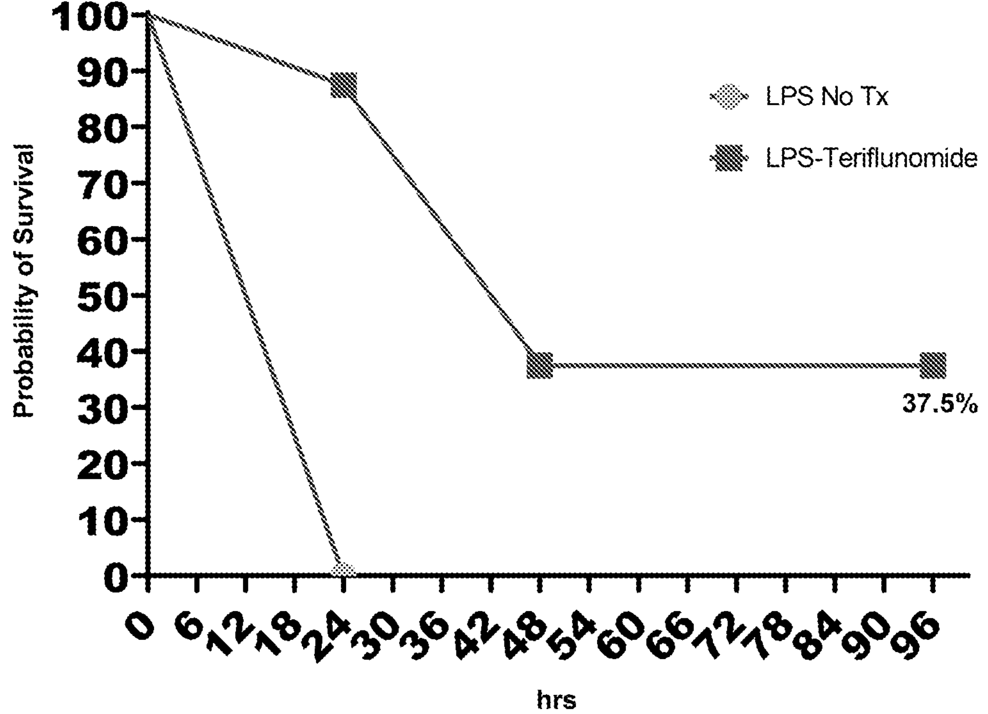
FIG. 20 is a graphical representation of the survival of LPS-treated animals following no treatment and treatment with teriflunomide. All of the animals were treated with 25 mg/kg of LPS IP. Kaplan-Meier survival in response to LPS administration. Comparison of the trend of survival curve was done using the log-rank (Mantel-Cox) test (recommended), and ** p<0.01.

A survival study was performed with sixteen animals per group of LPS-treated animals following no treatment and treatment with teriflunomide. The control group received 20 mg/kg of LPS i.p. and no treatment; whereas the teriflunomide group received 20 mg/kg of LPS and 4 mg of teriflunomide. None of the control animals lived up to 24 hours, whereas 6 of the teriflunomide treat animals lived out to 96 hours at which time they appeared normal. The P value for the difference was less than 0.0021. FIG. 20 is a graphical representation of the survival of LPS-treated animals following no treatment and treatment with teriflunomide. All of the animals were treated with 20 mg/kg of LPS i.p. Kaplan-Meier survival in response to LPS administration. Comparison of the trend of survival curve was done using the log-rank (Mantel-Cox) test (recommended), and ** $p<0.01$.

TABLE 1

| Comparison of Survival Curves | | |
|---|---|---|
| Log rank (Mantel-Cox) test | | |
| Chi square | 9.450 | |
| df | 1 | |
| P value | 0.0021 | |
| P value summary | ** | |
| Are the survival curves sig different? | Yes | |
| Median survival | | |
| LPS No Tx | 24.00 | |
| LPS-Teriflunomide | 48.00 | |
| Ratio (and its reciprocal) | 0.5000 | 2.000 |
| 95% CI of ratio | 0.1376 to 1.817<br>0.5504 to 7.267 | |

Example 8

In this Example, the embodiment of teriflunomide for use as a prophylaxis composition pre-exposure to an infectious agent that causes ALI or AKI or a cytokine storm was investigated. Two animals were analyzed per group of healthy controls, and LPS-treated animals following pre-treatment with teriflunomide, no treatment, and subsequent treatment with teriflunomide. The LPS was administered at 20 mg/kg and teriflunomide was administered at 4 mg/kg. A dose of teriflunomide was administered 24 hours before or 24 hours after the LPS dose. The kidneys from the animals in these groups were examined.

Figure 21:
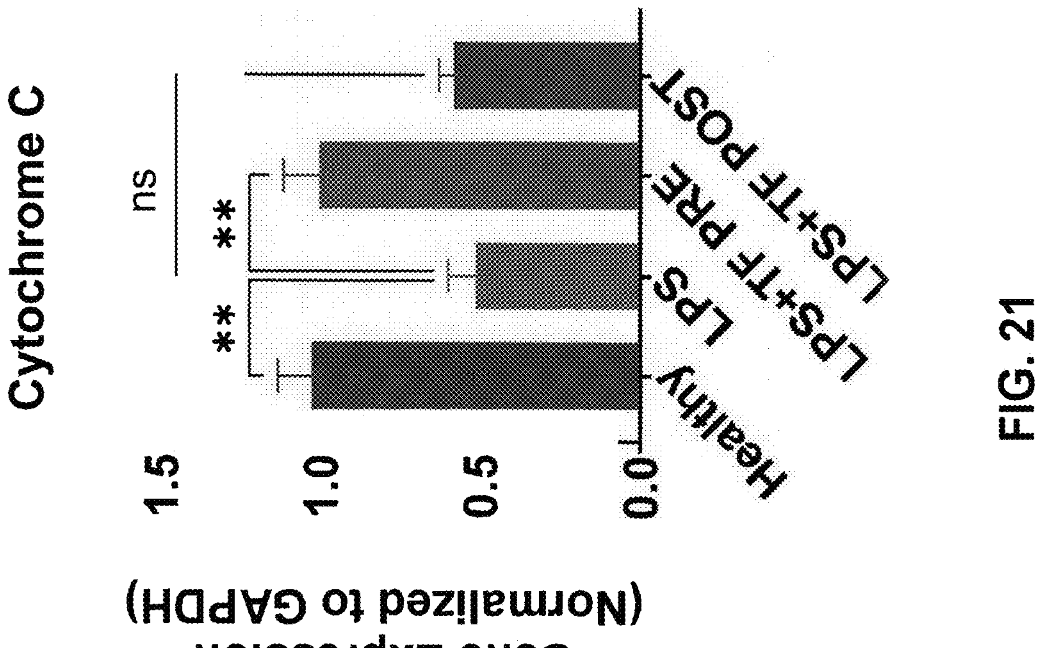
FIG. 21 is a graphical representation of gene expression of a kidney tissue-mitochondrial marker—cytochrome C (normalized to GAPDH) in healthy controls, and LPS-treated animals following pre-treatment with teriflunomide, no treatment, and subsequent treatment with teriflunomide, respectively. Data are the mean±SEM. ** p<0.01 and ns-no significance. 1-way ANOVA followed by a Dunnett's multiple comparisons test.

Cytochrome C, which is located in mitochondria and is importantly involved in ATP synthesis and energy metabolism, is a key marker of mitochondrial function. FIG. 21 is a graphical representation of gene expression of a kidney tissue-mitochondrial marker—cytochrome C (normalized to GAPDH) in healthy controls, and LPS-treated animals following pre-treatment with teriflunomide, no treatment, and subsequent treatment with teriflunomide, respectively. Data are the mean±SEM. ** $p<0.01$ and ns-no significance. 1-way ANOVA followed by a Dunnett's multiple comparisons test.

Figures 22A, 22B, 22C:
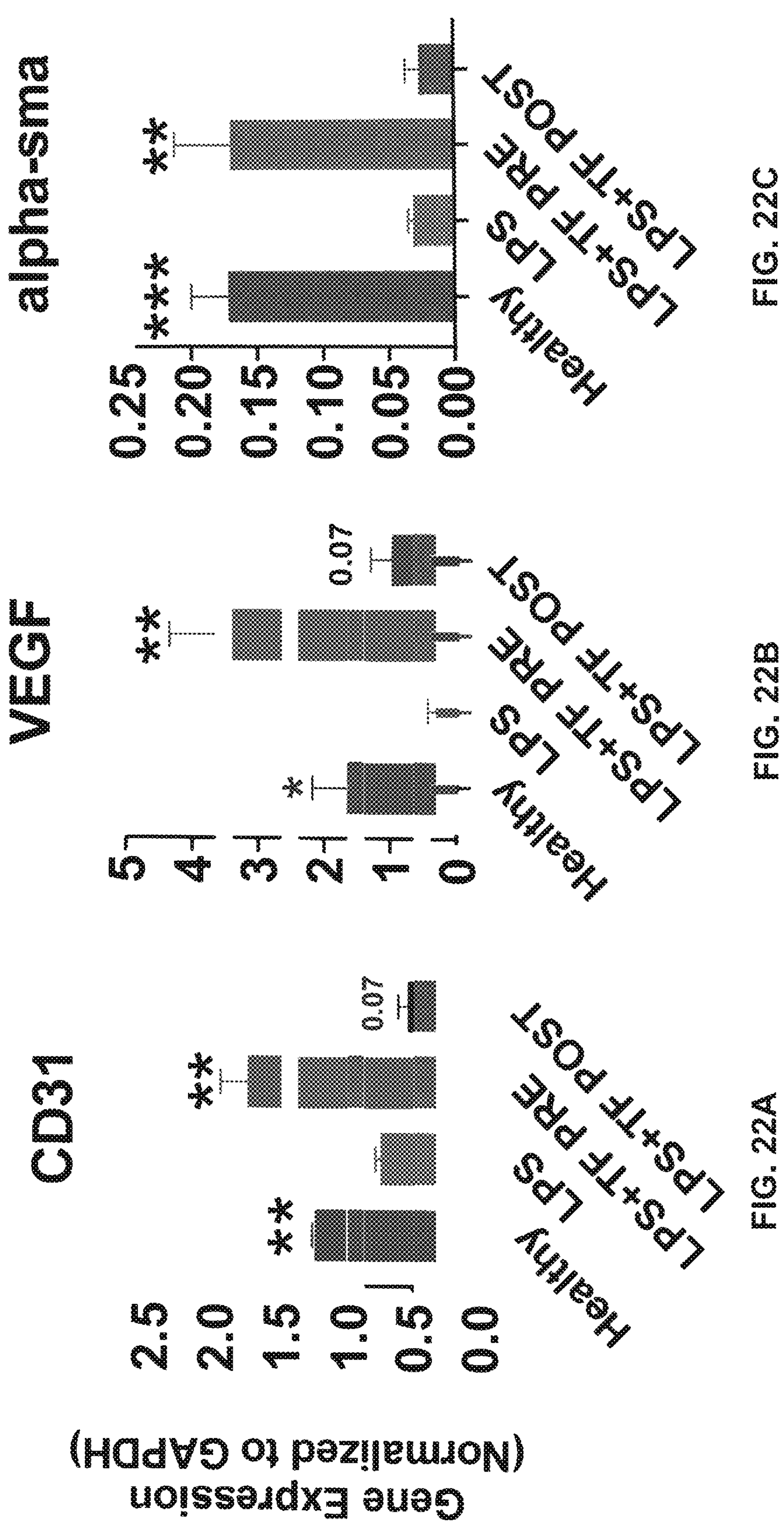
FIGS. 22A-22C are graphical representations of the relative gene expression of vascular markers in kidney tissue—CD31 (FIG. 22A), VEGF (FIG. 22B), and α-SMA (FIG. 22C) (normalized to GAPDH) in healthy controls, and LPS-treated animals following pre-treatment with teriflunomide, no treatment, and subsequent treatment with teriflunomide, respectively. Data are the mean±SEM. ** p<0.01 and ns-no significance. 1-way ANOVA followed by a Dunnett's multiple comparisons test.

CD31, also known as Pecan-1, is a marker for endothelial cells as it functions to prevent vascular leakage. VEGF promotes angiogenesis and is a marker for proliferating endothelium, while α-SMA is a marker of differentiation of the smooth muscle cells, which can be located in the vascular wall. Both serve as markers of healthy vascularity. FIGS. 22A-22C are graphical representations of the relative gene expression of vascular markers in kidney tissue—CD31 (FIG. 22A), VEGF (FIG. 22B), and α-SMA (FIG. 22C) (normalized to GAPDH) in healthy controls, and LPS-treated animals following pre-treatment with teriflunomide, no treatment, and subsequent treatment with teriflunomide, respectively. Data are the mean±SEM. ** $p<0.01$ and ns-no significance. 1-way ANOVA followed by a Dunnett's multiple comparisons test.

Figure 23:
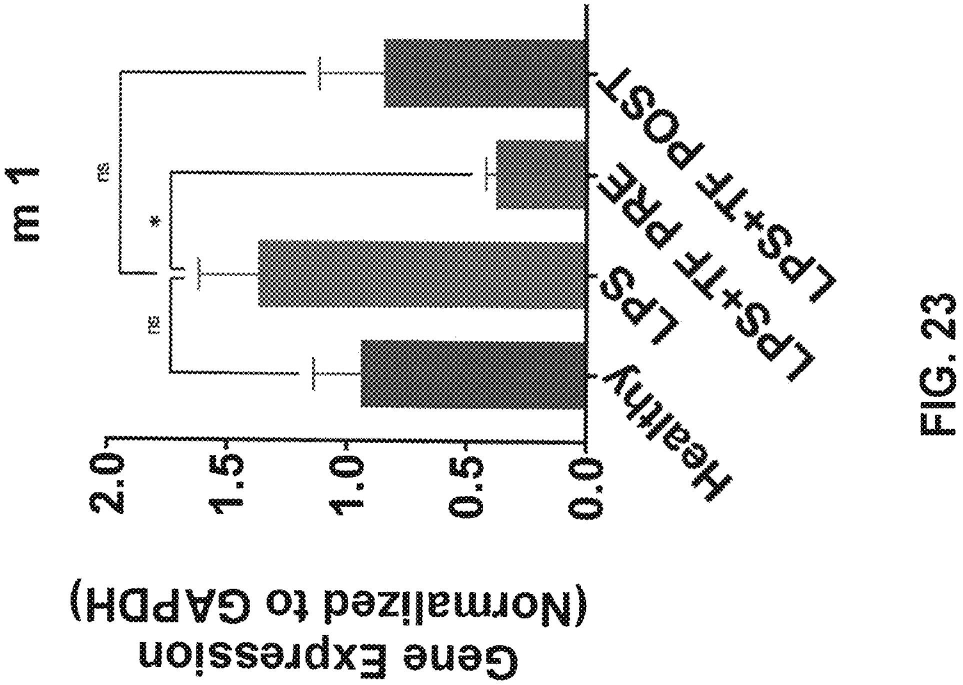
FIG. 23 is a graphical representation of gene expression of a kidney tissue injury marker—kim1 (normalized to GAPDH) in healthy controls, and LPS-treated animals following pre-treatment with teriflunomide, no treatment, and subsequent treatment with teriflunomide, respectively. Data are the mean±SEM. ** p<0.01 and ns-no significance. 1-way ANOVA followed by a Dunnett's multiple comparisons test.

Kim 1 is a phosphatidylserine receptor, which is involved in removal of apoptotic bodies, and is a renal injury marker. FIG. 23 is a graphical representation of gene expression of a kidney tissue injury marker—kim1 (normalized to GAPDH) in healthy controls, and LPS-treated animals following pre-treatment with teriflunomide, no treatment, and subsequent treatment with teriflunomide, respectively. Data are the mean±SEM. ** $p<0.01$ and ns-no significance. 1-way ANOVA followed by a Dunnett's multiple comparisons test.

Figure 24:
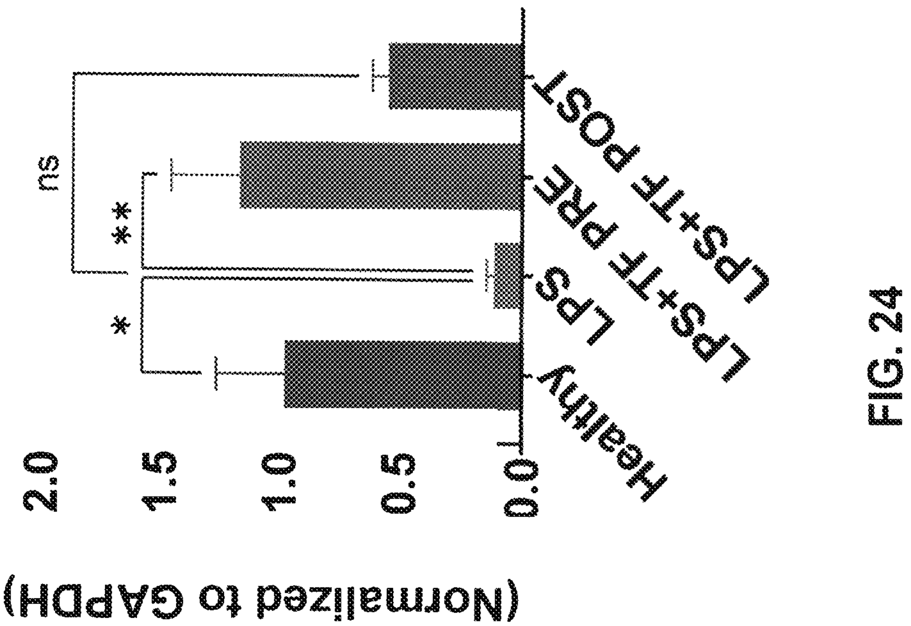
FIG. 24 is a graphical representation of gene expression of a kidney tissue-cell adhesion receptor—integrin B1 (normalized to GAPDH) in healthy controls, and LPS-treated animals following pre-treatment with teriflunomide, no treatment, and subsequent treatment with teriflunomide, respectively. Data are the mean±SEM. ** $p<0.01$ and ns-no significance. 1-way ANOVA followed by a Dunnett's multiple comparisons test.

Integrin beta-1 is a receptor for lamina and collagen in the kidney, and it contributes to capillary stability. FIG. 24 is a graphical representation of gene expression of a kidney tissue-cell adhesion receptor—integrin β1 (normalized to GAPDH) in healthy controls, and LPS-treated animals following pre-treatment with teriflunomide, no treatment, and subsequent treatment with teriflunomide, respectively. Data are the mean±SEM. ** $p<0.01$ and ns-no significance. 1-way ANOVA followed by a Dunnett's multiple comparisons test.

Example 9—Material and Methods

Experimental Design for IGF-1 and BTP-2 studies—The animal experiments involved B6 mice between 5-8 weeks of age. Most experiments involved five groups of animals: (1) healthy, (2) LPS untreated (LPS-No Tx), (3) IGF-I in vivo gene therapy one day before LPS injection (LPS+IGF-1), (4) BTP-2 16 mg/kg i.p. at the start of the study and the (5) combined therapy with IGF-I and BTP-2 (LPS-IGF-1+BTP-2). For the survival experiment, a lethal dose of LPS (25 mg/kg) was used and all of the untreated animals died by 72 hours. In the other experiments, a sublethal dose of LPS (20 mg/kg) was used.

LPS induced sepsis and subsequent AKI—Female C57BL/6 mice received a sublethal or lethal dose of LPS from *E. coli* (0127: B8 strain, Sigma Aldrich, St. Louis, MO, USA) in a concentration of 20 or 25 mg/kg body weight administrated in sterile PBS by intraperitoneal injection.

Treatment—In a preventive therapeutic strategy, some of the mice received an intramuscular injection of Lenti-IGF-1 24 hours before LPS injection; whereas, the calcium signaling blocker BTP-2 (16 mg/kg, Cayman Chemical) was administrated 1 hour before LPS injection. Some of the animals received a combination of Lenti-IGF-1 and BTP-2. Control group mice were injected with an equal volume of PBS.

Renal function assessment—Blood samples were collected through facial vein puncture at 48 hours The serum was separated by 3,000 rpm for 5 min at 4° C. Serum creatinine (CREA) were detected by Creatinine Assay Kit (Cayman Chemicals).

Measurements of mRNA Expression in the Kidney—For the measurement of the mRNA expressions of whole kidney tissue, we performed real-time PCR. The sequences of the primer and gene database numbers are listed in Table Si. The relative amount of mRNA was calculated using the comparative $C_t(\Delta\Delta C_t)$ method. All specific amplicons were normalized against GAPDH.

Vascular leakage permeability assay—Evans blue dye (EBD) was dissolved in a 0.9% saline solution at a concentration of 5 mg/mL and injected to the mouse tail vein (50 mg/kg, i.v.). After 30 min, the kidneys were harvested, dried, and weighed. Dried tissues were soaked in 3 mL of formamide and homogenized using a homogenizer followed by incubation at 60° C. for 18 hours The homogenized tissues were centrifuged at 12,000×g for 30 min. The absorbance of the supernatants was measured at 620 and 740 nm using a dual-wave ELISA plate reader.

Renal Histology—After sacrificing the mice, one part of the kidney was immediately cut, fixed in a 10% neutral buffered formalin solution, embedded in paraffin, and used for histopathological examination. 10-micrometer-thick sections were cut, deparaffinized, and hydrated. All renal serial sections were incubated at 4° C. overnight with one of two antibodies; rabbit polyclonal antibody against PECAM (CD31) (Santa Cruz, MA) or rabbit polyclonal antibody against α-SMA (Abcam, MA). After washing with TBST, biotinylated goat anti-rabbit IgG (1:200, Vector Labs, Burlingame, CA) were applied to the sections for 30 min at room temperature. Sections then were incubated with Streptavidin-HRP (Vector Labs, Burlingame, CA) for 30 min at room temperature. Diaminobenzidine (DAB; Vector Labs, Burlingame, CA) was used as the chromogen and hematoxylin as the counterstain. One part of the kidney was stained with periodic acid Schiff (PAS) stain. The PAS stained sections were examined for renal morphology in an automated fashion by quantification of a glycogen specific color in the kidney tissue using ImageJ (National Institutes of Health, Bethesda, MD, USA). A minimum of 10 fields for each kidney slide were examined and scored for pathological injury. A score from 0 to 4 was given for pathological assessment: 0, normal histology; 1, mild injury, 5% to 25% of tubules showed pathological damage; 2, moderate injury, 25% to 50% of tubules showed pathological damage; 3, severe injury, 50% to 75% showed pathological damage; and 4, almost all tubules in field of view were damaged. The average histological score for each sample was calculated. The images were captured with an Olympus BX51 microscope, 40× magnification. (Olympus, Center Valley, PA).

Acute Lung Injury Induced by LPS—Female C57BL/6 mice received a sublethal or lethal dose of LPS from *Escherichia coli* (0127: B8 strain, Sigma Aldrich, St. Louis, MO, USA). LPS in sterile PBS was administered intraperitoneally at 20- or 25-mg/kg body weight.

Treatment for Lung Studies-Lenti-IGF-I was administered intramuscularly 24 h before LPS injection. The TRP and ORAI calcium channel blocker BTP-2 (YM-58483 16 mg/kg, Cayman Chemical, Ann Arbor, MI, USA) was given IP 1 h before LPS injection. Some of the animals received a combination of lenti-IGF-I and BTP-2. Mice in control groups were injected with an equal volume of PBS.

Measurements of mRNA Expression in the Lungs—For the measurement of the mRNA expressions of the whole lung tissues, RT-qPCR was performed. Lung tissues were snap-frozen in liquid nitrogen. According to the manufacturer's instructions, total RNA was isolated using the RNeasy Micro Kit® (Qiagen, Valencia, CA, USA). First-strand cDNA was synthesized using the SuperScript® III Reverse Transcriptase (Life Technologies, Grand Island, NY, USA). Quantitative RT-qPCR was performed and analyzed in an Applied Biosystems 7900HT Real-Time PCR machine (Applied Biosystems, Foster City, CA). The PCR condition was 10 min at 95° C. followed by 40 cycles of 10 s at 95° C. and 15 s at 60° C. The relative amount of mRNA was calculated using the comparative Ct (DDCt) method. All specific amplicons were normalized against GAPDH. Table 2 (SEQ ID Nos:1-36) provides for a list of the primers.

TABLE 2

| Gene | Forward | Reverse |
|---|---|---|
| TLR-4 | GCCTTTCAGGGAATTAAGCTCC | GATCAACCGATGGACGTGTAAA |
| NFATC1 | GGAGAGTCCGAGAATCGAGAT | TTGCAGCTAGGAAGTACGTCT |
| TRPC6 | GCTTCCGGGGTAATGAAAACA | GTATGCTGGTCCTCGATTAGC |
| TRPC3 | GCCTTCATGTTCGGTGCTC | GGTCACCTCCAGATGCTCATT |

TABLE 2-continued

| Gene | Forward | Reverse |
|---|---|---|
| ORAI 1 | CTCAACTCGGTCAAAGAGTCAC | CACGACCTCTGCTAGGAAAAG |
| CALCINEURIN | GTGAAAGCCGTTCCATTTCCA | GAATCGAAGCACCCTCTGTTATT |
| IL-1B | GAAATGCCACCTTTTGACAGTG | TGGATGCTCTCATCAGGACAG |
| IL-17 | GGCCCTCAGACTACCTCAAC | TCTCGACCCTGAAAGTGAAGG |
| IL-6 | CTGCAAGAGACTTCCATCCAG | AGTGGTATAGACAGGTCTGTTGG |
| TNF-A | CCTGTAGCCCACGTCGTAG | GGGAGTAGACAAGGTACAACCC |
| IFN-g | ATGAACGCTACACACTGCATC | CCATCCTTTTGCCAGTTCCTC |
| CD-31 | CTGCCAGTCCGAAAATGGAAC | CTTCATCCACCGGGGCTATC |
| VEGF | GCACATAGAGAGAATGAGCTTCC | CTCCGCTCTGAACAAGGCT |
| A-SMA | GTCCCAGACATCAGGGAGTAA | TCGGATACTTCAGCGTCAGGA |
| SP-D | CTCCCACTATCAGAAAGCTGC | CCCACATCTGTCATACTCAGGAA |
| CASPASE 3 | ATGGAGAACAACAAAACCTCAGT | TTGCTCCCATGTATGGTCTTTAC |
| NGAL | GGGAAATATGCACAGGTATCCTC | CATGGCGAACTGGTTGTAGTC |
| GAPDH | TGGCCTTCCGTGTTCCTAC | GAGTTGCTGTTGAAGTCGCA |

Notes:

TLR-4: Toll-like receptor 4, NFATC1: Nuclear factor of activated T cells 1; TRPC3: Transient receptor potential cation channel subfamily C member 3, TRPC6: Transient receptor potential cation channel subfamily C member 6, ORAI-1: ORAI calcium release-activated calcium modulator 1, IL-1B: Interleukin 1 beta, IL-17: Interleukin 17; IL-6: Interleukin-6; TNF-α: Tumor Necrosis Factor-α, IFN-g: Interferon Gamma, CD-31: Platelet/endothelial cell adhesion molecule 1, VEGF: Vascular endothelial growth factor, a-SMA: Alpha Smooth Muscle actin, NGAL: Lipocalin 2; GAPDH: Glyceraldehyde-3- Phosphate Dehydrogenase.

Lung Immunocytochemistry—After the mice were sacrificed, one part of the lung was immediately cut, fixed in a 10% neutral-buffered formalin solution, embedded in paraffin, and used for histopathological examination. Ten-micrometer-thick sections were cut, deparaffinized, and hydrated. All lung serial sections were incubated at 4° C. overnight with one of two antibodies: rabbit polyclonal antibody against PECAM (CD31) (Santa Cruz Biotechnology, Dallas, TX, USA) or rabbit polyclonal antibody against α-SMA (Abcam, Cambridge, MA, USA). After washing, biotinylated goat anti-rabbit IgG (1:200, Vector Labs, Burlingame, CA, USA) were applied to the sections for 30 min at room temperature. Lung sections were incubated with Streptavidin-HRP (Vector Labs, Burlingame, CA, USA) for 30 min at room temperature. Diaminobenzidine (DAB; Vector Labs, Burlingame, CA, USA) was used as the chromogen and hematoxylin as the counterstain.

Lung Histology and Histologic Score—Tissue sections from 1 portion of the lung were stained with hematoxylin and eosin (H&E) staining. The H&E-stained sections were examined for lung morphology using ImageJ (National Institutes of Health, Bethesda, MD, USA). A minimum of 10 fields for each lung slide was examined and scored for pathological injury. The average histological score for each sample was calculated based on four histological parameters: linear intercept, septal thickness, area disrupted, and destructive index. The images were captured with an Olympus BX51 microscope, 40× magnification (Olympus, Center Valley, PA, USA).

Statistical Analysis—Statistical analyses were performed with GraphPad software (Prism 5.02, San Diego, CA, USA). The quantitative analyses, such as qPCR data, were reported as the mean±SEM and analyzed using 1- or 2-way ANOVA, followed by a Dunnett's multiple comparisons test or a Bonferroni post-hoc analysis and unpaired t-test. Evaluation of the histopathology preparations was blind, and specimen identity was revealed only after completion of the analyses. A p-value of $<0.05$ was considered to be statistically significant.

Differentiation Of HL-60 To Neutrophil By Vitamin A (ATRA), Macrophages By 1,25(OH)2D3 And To Monocyte By PMA-HL60 cells were seeded at $2.5\times10^5$ cells/ml as 4 ml cultures in 25 $cm^2$ flasks. Neutrophils differentiation was induced by adding a 100 nM ATRA (Vitamin A) to $5\times10^5$ HL60 cells/ml for 72 h in RPMI cell culture media. For Macrophage differentiation, a 100 nM of 1,25(OH)2 D3 was added to the culture. For Monocytic cell differentiation HL-60 cells ($2\times10^5$/mL) were cultured in the presence of 40 nM phorbol 12-myristate 13-acetate (PMA, Cell Signaling, Danvers, MA, USA). On day 2-3, cells were re-fed. The first signs of differentiation appeared on day 3. On day 5 a complete differentiation was apparent.

Validation Of Neutrophil, Macrophage And Monocytic Cellular Differentiation—After cells counting, $2\times10^6$ cells per sample were stained with viability dye (Life Technologies) according the manufacturer's instructions. Cells were incubated in blocking solution containing 5% normal mouse serum, 5% normal rat serum, and 1% FcBlock (eBiosciences, San Diego, CA) in PBS and then stained with a standard panel of immunophenotyping antibodies for neutrophils (CD11B, Ly6G), macrophages (CD11B/MAC-1) and ((CD11B/CD14) for 30 minutes at room temperature. After staining, cells were washed and fixed with 0.4% paraformaldehyde in PBS. Data was acquired with a BD FACSAria™ flow cytometer software (BD Bioscience). Data was analyzed using Flowjo v10.

Cytokine Stimulation With LPS And Treatment With Teriflunomide—HL60 derived Neutrophils and macrophages were re-suspended in RPMI 1640 medium containing 10% (w/v) fetal bovine serum plus penicillin/streptomycin and plated into 96-well plates at a density of 1×104 cells/well. Cells were treated with 10 ng/mL lipopolysaccharide (LPS; Sigma-Aldrich) plus Teriflunomide at various concentrations (0, 10, 25, and 50 μM). Controls included LPS stimulant alone (positive controls) or no stimulant (negative controls). After overnight incubation at 37° C. in a 5% CO2 atmosphere, cells were harvested and stored at—80° C. for RNA extraction or used for Flow cytometry. An effective dose of teriflunomide was used to determine if teriflunomide inhibits the differentiation of HL 60 cells to macrophages.

Teriflunomide Effect On LPS Induced Cytokine Storm—After cytokine stimulation with LPS and subsequent treatment with Teriflunomide, an assay was performed to assess the inhibition of cytokine storm by evaluation of expression for marker such as IL-6, TNF-α, IFN-g, IL-1b, IL-2, IL-4, IL-8, IL-1β, IL-12 by multichromatic flow cytometry. After cells counting, $2\times10^6$ cells per sample were stained with Aqua Live/Dead viability dye (Life Technologies) according the manufacturer's instructions. Expressions of cell surface and intracellular proteins were analyzed by fluorescence-activated cell sorting (FACS). In brief, ~0.5-1×106 cells in 100 μl FACS buffer (PBS containing 1% fetal bovine serum and 0.05% sodium azide) were stained with fluorescence-conjugated antibodies specific for the desired cell surface marker such as CD11B+Ly6G (For neutrophils), CD11B+MAC-1 (For macrophages) and CD11B+CD14 (for monocytes) at 4-C for 30 min. The cells were then stained with fluorescence-conjugated antibodies specific for the desired intracellular proteins (Cytokines) at 4-C for 30 min in the permeabilization buffer (e.g., Perm/Wash buffer; BD Biosciences, San Jose, CA, USA). Finally, the cells were washed twice in the permeabilization buffer and twice in the FACS buffer before being analyzed on a FACSAria II cytometer (BD Biosciences). Data was acquired with a BD FACSAria™ flow cytometer software (BD Bioscience). Data was analyzed using Flowjo.v10.

Teriflunomide effect on LPS induced calcium signaling—After cytokine stimulation with LPS and subsequent treatment with Teriflunomide an assay was performed to assess the effects on the RNA and protein expression of calcium signaling regulators. For mRNA quantification, total RNA will be extracted from HL60 derived neutrophils and macrophages using RNeasy mini kit Plus (Qiagen) according to the manufacturer's instructions. The obtained RNA was reverse-transcribed with a Reverse Transcriptase. Subsequently, the resultant cDNA was amplified using SYBR Green qPCR master mix (Applied Biosystems Inc., Carlsbad, CA). Quantitative real-time PCR was performed on an ABI 7500 real-time PCR system (Applied Biosystems Inc., Carlsbad, CA) using the following parameters: initial denature at 95° C. for 10 min, followed by 40 cycles of 15 s at 95° C. and 1 min at 60° C. List of the primers for calcium channel regulator is list below (Park and others, 2016). Glyceraldehyde-3-phosphate dehydrogenase (GAPDH) was used as an internal control for quantitative analysis. The data were analyzed using the critical threshold (ACT) and the comparative critical threshold (ΔΔCT) methods in the AB-7500 software.

Statistical analysis—Statistical analyses were performed with GraphPad software (Prism 5.02). Kaplan Meier survival studies were analyzed using the Log-rank test and Gehan-Breslow-Wilcoxon test. The quantitative analysis such as Q-PCR data are reported as the mean±SEM and were analyzed using 1- or 2-way ANOVA followed by a Dunnett's multiple comparisons test or a Bonferroni post hoc analysis as appropriate, or unpaired t test. Evaluation of histopathology preparations was blind, and specimen identity was revealed only on completion of analysis. A P-value of $<0.05$ was considered to be statistically significant.

The foregoing description generally illustrates and describes various embodiments. It will, however, be understood by those skilled in the art that various changes and modifications can be made without departing from the spirit and scope of the technology as disclosed herein, and that it is intended that all matter contained in the above description or shown in the accompanying drawings shall be interpreted as being illustrative, and not to be taken in a limiting sense. Accordingly, various features and characteristics as discussed herein may be selectively interchanged and applied to other illustrated and non-illustrated embodiments, and numerous variations, modifications, and additions further can be made thereto without departing from the spirit and scope of the embodiments as set forth in the appended claims.

What is claimed is:

1. A method for treating acute lung injury and/or acute kidney injury in a subject-experiencing a cytokine storm, the method comprising:

Administering to the subject a therapeutically effective amount of IGF-1 and an agent to decrease cytosolic calcium, wherein the agent to decrease cytosolic calcium is selected from among an anti-CRAC channel antibody, 3,5-bis(trifluoromethyl) pyrazole derivative (BTP-2), 2-Aminoethoxydiphenyl borate (2-APB), and/or teriflunomide.

2. The method of claim 1 that results in a reduction of two or more proinflammatory cytokines and an increase in a vascular integrity gene.

3. The method of claim 2, wherein the two or more proinflammatory cytokines are interferon-y and interleukin-17.

4. The method of claim 2, wherein the vascular integrity gene is CD-31 or α-SMA.

* * * * *